(12) United States Patent
Duan et al.

(10) Patent No.: US 10,099,998 B2
(45) Date of Patent: Oct. 16, 2018

(54) COMPOUND, AND SEPARATION METHOD, SYNTHESIS METHOD AND USE THEREOF

(71) Applicant: BEIJING PEKING UNIVERSITY WBL BIOTECH CO., LTD., Beijing (CN)

(72) Inventors: Zhenwen Duan, Beijing (CN); Shuren Guo, Beijing (CN); Xuemei Li, Beijing (CN)

(73) Assignee: BEIJING PEKING UNIVERSITY WBL BIOTECH CO., LTD., Beijing (CN)

( * ) Notice: Subject to any disclaimer, the term of this patent is extended or adjusted under 35 U.S.C. 154(b) by 0 days.

(21) Appl. No.: 15/548,760

(22) PCT Filed: Jan. 27, 2016

(86) PCT No.: PCT/CN2016/072306
§ 371 (c)(1),
(2) Date: Aug. 3, 2017

(87) PCT Pub. No.: WO2016/124087
PCT Pub. Date: Aug. 11, 2016

(65) Prior Publication Data
US 2018/0022688 A1  Jan. 25, 2018

(30) Foreign Application Priority Data

Feb. 4, 2015 (CN) .......................... 2015 1 0058282

(51) Int. Cl.
| | |
|---|---|
| *C07C 69/02* | (2006.01) |
| *A61K 31/23* | (2006.01) |
| *C07C 69/73* | (2006.01) |
| *C07C 67/03* | (2006.01) |
| *C07C 67/56* | (2006.01) |
| *A61K 31/216* | (2006.01) |
| *C07C 67/48* | (2006.01) |

(52) U.S. Cl.
CPC .............. *C07C 69/73* (2013.01); *C07C 67/03* (2013.01); *C07C 67/56* (2013.01); *A61K 31/216* (2013.01); *C07C 67/48* (2013.01); *C07C 2602/10* (2017.05)

(58) Field of Classification Search
CPC ....... C07C 69/02; C07C 53/126; A61K 31/23; A61K 31/191
USPC .......... 560/130, 129; 562/512; 514/552, 557
See application file for complete search history.

(56) References Cited

U.S. PATENT DOCUMENTS

2004/0138294 A1  7/2004  Grahek et al.

OTHER PUBLICATIONS

International Search Report issued in connection with corresponding International Application No. PCT/CN2016/072306, dated May 4, 2016. 2 pages.
Iwabuchi, Haruo et al., "Studies on Drug Metabolism Using Liquid Chromatography/Mass Spectrometry: Comparison of Three Liquid Chromatographic/Mass Spectrometric Interfaces," Biological Mass Spectrometry, vol. 23, 540-546 (1994).
Search Report and Written Opinion issued in connection with corresponding Singapore Application No. 11201706353W, dated May 5, 2018. 3 pages.
Muramatsu, S. et al., "Metabolism of Pravastatin Sodium by 3α-Hydroxysteroid Dehydrogenase,". *Biological & Pharmaceutical Bulletin*, Nov. 30, 1997, vol. 20, No. 11, pp. 1199-1203.

*Primary Examiner* — Charanjit Aulakh
(74) *Attorney, Agent, or Firm* — Kilpatrick Townsend & Stockton LLP

(57) ABSTRACT

The invention relates to new compounds as well as a separation method, a synthetic method and use thereof. It is demonstrated by an assay on activity that the compound has an activity of inhibiting an HMG-CoA reductase. In addition, the invention also relates to a derivative of the compound.

34 Claims, 1 Drawing Sheet

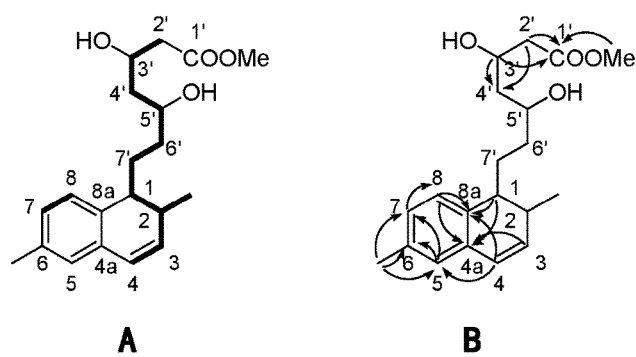
The ¹H-¹H COSY(—) (Fig. 1A) and HMBC signals ( ⌒ ) (Fig. 1B) of Compound 5

COMPOUND, AND SEPARATION METHOD, SYNTHESIS METHOD AND USE THEREOF

CROSS-REFERENCE TO RELATED APPLICATIONS

This application is a national stage application under 35 U.S.C. § 371 of International Patent Application No. PCT/CN2016/072306, filed Jan. 27, 2016, which claims priority to Chinese Application No. 201510058282.5, filed Feb. 4, 2015.

TECHNICAL FIELD

The invention relates to new compounds separated from *Monascus*-fermented rice, as well as a separation method, a synthetic method and a use thereof. It is demonstrated by an assay on activity that the compound has an activity of inhibiting an HMG-CoA reductase. In addition, the invention also relates to compounds structurally similar to the compound, and a synthetic method thereof.

BACKGROUND ART

Traditional Chinese medicines have been used and studied for a long time. *Monascus*-fermented rice refers to a purple rice-koji prepared by fermentation of rice as raw material with *Monascus*. *Monascus*-fermented rice has been used in China since Han dynasty. In 1970s, Professor Endo from Japan separated the physiologically active substance monacolin K from *Monascus ruber*. Since then, many researchers both at home and abroad have discovered physiologically active substances from the metabolites of *Monascus* constantly, including monacolin compounds, *Monascus* pigments, a hypotensive ingredient GABA, an antioxidant ingredient dimerumic acid, and so on. There is still much potential in research and development of *Monascus*-fermented rice.

Xuezhikang (capsule or tablet), a *Monascus*-fermented rice preparation, is a lipid-regulatory Chinese drug developed by the applicant and commercially available in China, is rich in multiple active ingredients such as statins, and has less adverse reactions compared to the existing lipid-regulatory chemical drugs. Its indications refer to cardiovascular and cerebrovascular diseases caused by hyperlipidemia and atherosclerosis. Xuezhikang is effective in eliminating dampness and dispelling phlegm, activating blood and removing blood stasis, fortifying the spleen and promoting digestion. Xuezhikang is applied to short breath, acratia, dizziness, headache, oppression in chest, abdominal distension, and anorexia of spleen deficiency and phlegm blockade syndrome; hyperlipidemia; or adjunctive treatment of cardiovascular and cerebrovascular diseases caused by hyperlipidemia and atherosclerosis.

By studying Xuezhikang using the existing technologies, the following ingredients are separated therefrom:

Statin Ingredients

Xuezhikang is rich in natural statins.

Isoflavone Ingredients

Xuezhikang further comprises isoflavones, sterol substances, more than 20 amino acids, unsaturated fatty acids and multiple trace elements. Isoflavone ingredients mainly comprise genistein, daidzein, and glycitein, all of which belong to isoflavones.

Sterol Ingredients

Phytosterin refers to a substance having a structure similar to that of cyclic alcohol, is widely distributed in nature, and represents the final product of plant metabolism.

Sterols in Xuezhikang include ergosterol, stigmasterol, sitosterol and the like.

Amino Acid Ingredients

Xuezhikang comprises more than 20 amino acid ingredients such as glycerin, proline, serine, aspartic acid, glutamic acid, arginine, histidine, taurine, and γ-aminobutyric acid (GABA).

Unsaturated Fatty Acid Ingredients

Xuezhikang comprises fatty acid ingredients in a large amount. The methyl-esterified derivatives of the fatty acids in Xuezhikang were studied by gas chromatography-mass spectrum technology, and 14 fatty acid ingredients were identified, among which palmitic acid, linoleic acid and oleic acid were comprised in a large amount.

Trace Element Ingredients

Xuezhikang mainly comprises trace elements such as Mg and Se, wherein the Mg content is relatively high.

SUMMARY OF INVENTION

One object of the invention is to provide a compound of Formula (I) or a stereoisomer, tautomer, racemate, metabolite, prodrug, pharmaceutically acceptable salt or solvate thereof:

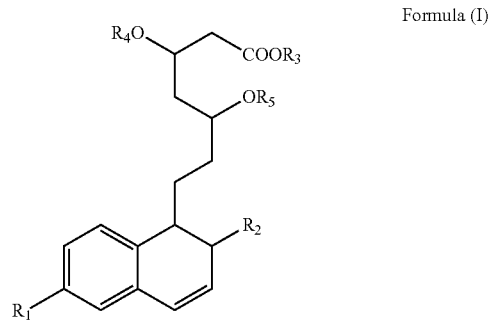

Formula (I)

wherein $R_1$ is selected from H, $C_1$-$C_6$ alkyl, halo $C_1$-$C_6$ alkyl, $(CH_2)_{1-6}OH$, $C_3$-$C_7$ cycloalkyl, halo $C_3$-$C_7$ cycloalkyl, $C_1$-$C_6$ alkoxy, halo $C_1$-$C_6$ alkoxy, $C_1$-$C_6$ alkylthio, halo $C_1$-$C_6$ alkylthio, halogen, nitro, amino and cyano;

$R_2$ is selected from H, $C_1$-$C_6$ alkyl, halo $C_1$-$C_6$ alkyl, $(CH_2)_{1-6}OR_6$, $C_3$-$C_7$ cycloalkyl, halo $C_3$-$C_7$ cycloalkyl, $C_1$-$C_6$ alkoxy, halo $C_1$-$C_6$ alkoxy, $C_1$-$C_6$ alkylthio, halo $C_1$-$C_6$ alkylthio, halogen, nitro, amino and cyano;

$R_3$ is selected from H and $C_1$-$C_6$ alkyl;

$R_4$ and $R_5$ each are independently selected from: H, $-COR_7$, $-SO_2R_8$, and $-SiR_9R_{10}R_{11}$;

wherein, $R_7$ is selected from $C_1$-$C_6$ alkyl and halo $C_1$-$C_6$ alkyl; $R_8$ is selected from $C_1$-$C_6$ alkyl, optionally substituted $C_1$-$C_6$ alkyl, $C_6$-$C_{10}$ aryl, and optionally substituted $C_6$-$C_{10}$ aryl; $R_9$, $R_{10}$ and $R_{11}$ are independently selected from $C_1$-$C_6$ alkyl;

wherein, $R_6$ has the same definition as $R_4$ and $R_5$;

wherein, the compound of Formula (I) wherein $R_1$ is $(CH_2)OH$, $R_2$ is methyl, and $R_3$, $R_4$ and $R_5$ are H, is excluded.

Another object of the invention is to provide a method for preparing the compound of Formula (I) according to the invention:

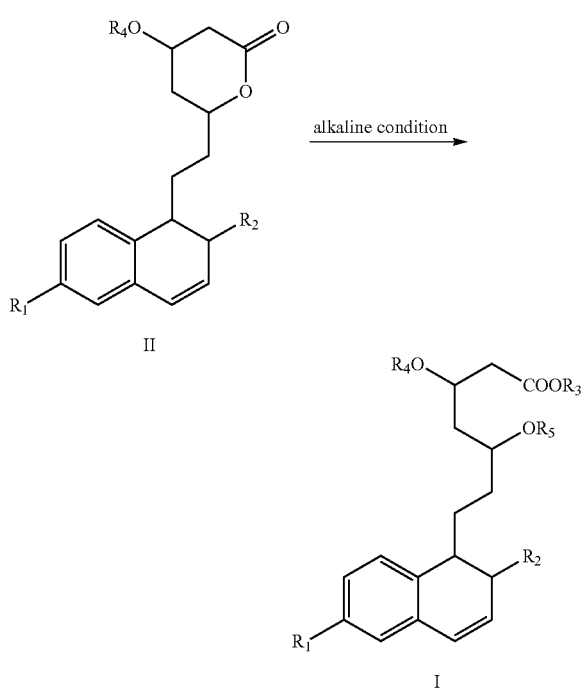

reacting a compound of Formula (II) under alkaline condition, or adding an esterification reagent under alkaline condition, to prepare the compound of Formula (I). In Formula (II), $R_1$, $R_2$, and $R_4$ have the same meanings as defined in Formula (I).

The pH range of the alkaline condition is 7.5-14, and optionally, an alkaline reagent such as sodium hydroxide, potassium hydroxide, ammonia water and sodium carbonate, or a solvent may be added. The esterification reagent may be selected from lower alcohol such as methanol and ethanol; anhydride (acetic anhydride, sulfonic anhydride, trifluormethane sulfonic anhydride, etc.), acyl chloride (toluene sulfonyl chloride), and chlorosilane (tert-butyldimethylchlorosilane).

Another object of the invention is to provide a method for extracting Compound 5 from *Monascus*-fermented rice or extract thereof, comprising the following steps of:

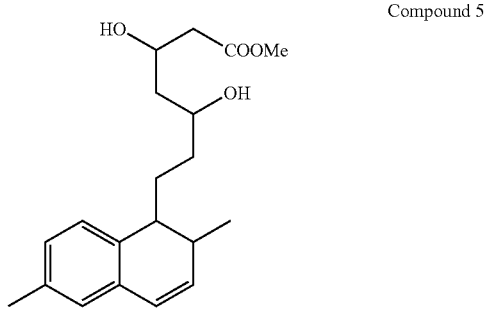 [SMILES: COC(=O)CC(O)CC(O)CCC1c2ccc(C)cc2C=CC1C]

Compound 5

1) extracting *Monascus*-fermented rice or extract thereof with ethyl acetate (or dichloromethane or methanol or ethanol, or methanol/ethanol aqueous solution) as a solvent;
2) separating the ethyl acetate (or dichloromethane or methanol or ethanol, or methanol/ethanol aqueous solution) extract obtained in Step 1) by silica gel column chromatography, and carrying out gradient elution with petroleum ether, ethyl acetate and methanol, to obtain the ethyl acetate eluting fraction;
3) separating the ethyl acetate eluting fraction obtained in Step 2) by silica gel column chromatography, carrying out elution with dichloromethane-ethyl acetate-methanol, analyzing and combining the fractions, to obtain 5 fractions in Step 3);
4) separating the second fraction obtained in Step 3) by C18 column chromatography, and carrying out gradient elution with acetonitrile-methanol-water, to obtain 82% (acetonitrile-methanol 1:1) aqueous solution eluting fraction;
5) further separating the 82% (acetonitrile-methanol 1:1) aqueous solution eluting fraction obtained in Step 4) by sephadex LH-20 column chromatography using dichloromethane-methanol as a mobile phase, and analyzing and combining the fractions to obtain 6 fractions in Step 5); and
6) purifying the third fraction obtained in Step 5) by chromatography using acetonitrile-methanol-water as a mobile phase and using C18 chromatographic column as a stationary phase, to obtain Compound 5.

Another object of the invention is to provide a pharmaceutical composition, comprising at least one compound according to invention and optionally, a pharmaceutically acceptable excipient.

Another object of the invention is to provide use of the compound according to the invention or a pharmaceutical composition comprising the compound in the manufacture of a medicament, in particular a medicament for inhibiting HMG-CoA reductase. Correspondingly, the invention provides a method for preventing and/or treating dyslipidemia, hyperlipemia, or atherosclerosis in a patient, comprising administering a therapeutically effective amount of at least one compound of the invention to the patient in need of treatment. Dyslipidemia refers to a condition in which one or more blood lipid-associated indexes in human body do not fall into the corresponding normal ranges, including elevated total cholesterol, elevated low density lipoprotein cholesterol, elevated apolipoprotein B, elevated triglyceride, and the like. The invention provides a method for preventing and/or treating hypercholesterolemia, combined hyperlipidemia in a patient, comprising administering a therapeutically effective amount of at least one compound of the invention to the patient in need of treatment.

The invention provides a method for treating an increase in total cholesterol, an increase in low density lipoprotein cholesterol, an increase in apolipoprotein B, an increase in triglyceride and the like when the effect of a lifestyle intervention therapy (such as diet adjustment, body weight control, more exercise, and quitting smoking) is not satisfactory.

In said uses, the compound of the invention can be used alone, or in combination with an effective amount of additional lipid-regulatory drug(s). The additional lipid-regulatory drug includes cholesterol synthesis inhibitors (statins or salts thereof, such as lovastatin, pravastatin, simvastatin, fluvastatin, atorvastatin, and pitavastatin), cholesterol absorption inhibitors (Ezetimibe and the like), fibrates (Lopid, lipanthyl ciprofibrate, bezafibrate, fenofibrate and gemfibrozil), nicotinic acids (nicotinic acid, inositol nicotinate, Dongzhiping, and niceritrol), bile acid sequestrants, and phenoxy aromatic acids.

The compound according to the invention or a pharmaceutically acceptable salt thereof (such as acetate, malonate, tartrate, succinate, hydro chlorate, sulfate, and nitrate), may be used to prevent or treat said diseases.

DESCRIPTION OF THE DRAWINGS

FIG. 1 shows the $^1$H-$^1$H COSY(-) (FIG. 1A) and HMBC signals ( ⌒ ) (FIG. 1B) of Compound 5 according to the invention.

SPECIFIC MODES FOR CARRYING OUT THE INVENTION

The invention relates to a compound of Formula (I), or a stereoisomer, tautomer, racemate, metabolite, prodrug, pharmaceutically acceptable salt or solvate thereof:

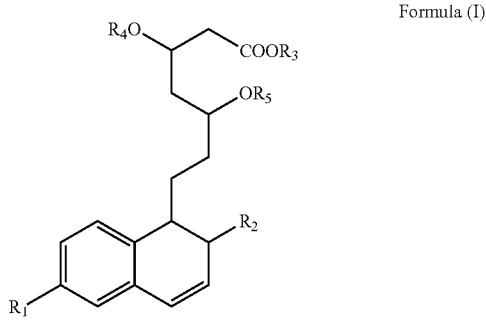

Formula (I)

$R_1$ is selected from H, $C_1$-$C_6$ alkyl, halo $C_1$-$C_6$ alkyl, $(CH_2)_{1-6}$OH, $C_3$-$C_7$ cycloalkyl, halo $C_3$-$C_7$ cycloalkyl, $C_1$-$C_6$ alkoxy, halo $C_1$-$C_6$ alkoxy, $C_1$-$C_6$ alkylthio, halo $C_1$-$C_6$ alkylthio, halogen, nitro, amino and cyano;

$R_2$ is selected from H, $C_1$-$C_6$ alkyl, halo $C_1$-$C_6$ alkyl, $(CH_2)_{1-6}$OR$_6$, $C_3$-$C_7$ cycloalkyl, halo $C_3$-$C_7$ cycloalkyl, $C_1$-$C_6$ alkoxy, halo $C_1$-$C_6$ alkoxy, $C_1$-$C_6$ alkylthio, halo $C_1$-$C_6$ alkylthio, halogen, nitro, amino and cyano;

$R_3$ is selected from H and $C_1$-$C_6$ alkyl;

$R_4$ and $R_5$ each are independently selected from: H, —COR$_7$, —SO$_2$R$_8$, and —SiR$_9$R$_{10}$R$_{11}$;

wherein, $R_7$ is selected from $C_1$-$C_6$ alkyl and halo $C_1$-$C_6$ alkyl; $R_8$ is selected from $C_1$-$C_6$ alkyl, optionally substituted $C_1$-$C_6$ alkyl, $C_6$-$C_{10}$ aryl, and optionally substituted $C_6$-$C_{10}$ aryl; $R_9$, $R_{10}$ and $R_{11}$ are independently selected from $C_1$-$C_6$ alkyl;

wherein, $R_6$ has the same definition as $R_4$ and $R_5$;

wherein, the compound of Formula (I) wherein $R_1$ is $(CH_2)$OH, $R_2$ is methyl, and $R_3$, $R_4$ and $R_5$ are H, is excluded.

In one embodiment, the invention relates to a compound of Formula (I), wherein, $R_1$ is selected from H, $C_1$-$C_3$ alkyl, halo $C_1$-$C_3$ alkyl, $(CH_2)_{1-3}$OH, $C_3$-$C_6$ cycloalkyl, halo $C_3$-$C_6$ cycloalkyl, $C_1$-$C_3$ alkoxy, halo $C_1$-$C_3$ alkoxy, $C_1$-$C_3$ alkylthio, halo $C_1$-$C_3$ alkylthio, halogen, nitro, amino and cyano.

In one embodiment, the invention relates to a compound of Formula (I), wherein, $R_1$ is selected from H, $C_1$-$C_3$ alkyl, halo $C_1$-$C_3$ alkyl, $(CH_2)_{1-3}$OH, halogen, nitro, amino and cyano.

In one embodiment, the invention relates to a compound of Formula (I), wherein, $R_1$ is selected from H, $C_1$-$C_3$ alkyl, and $(CH_2)_{1-3}$OH.

In one embodiment, the invention relates to a compound of Formula (I), wherein $R_2$ is selected from H, $C_1$-$C_3$ alkyl, halo $C_1$-$C_3$ alkyl, $(CH_2)_{1-3}$OR$_6$, $C_3$-$C_6$ cycloalkyl, halo $C_3$-$C_6$ cycloalkyl, $C_1$-$C_3$ alkoxy, halo $C_1$-$C_3$ alkoxy, $C_1$-$C_3$ alkylthio, halo $C_1$-$C_3$ alkylthio, halogen, nitro, amino and cyano;

wherein, $R_6$ is selected from H, —COR$_7$, —SO$_2$R$_8$, and —SiR$_9$R$_{10}$R$_{11}$;

wherein, $R_7$ is selected from $C_1$-$C_6$ alkyl and halo $C_1$-$C_6$ alkyl; $R_8$ is selected from $C_1$-$C_6$ alkyl, optionally substituted $C_1$-$C_6$ alkyl, $C_6$-$C_{10}$ aryl, and optionally substituted $C_6$-$C_{10}$ aryl; $R_9$, $R_{10}$ and $R_{11}$ are independently selected from $C_1$-$C_6$ alkyl.

In one embodiment, the invention relates to a compound of Formula (I), wherein $R_2$ is selected from H, $C_1$-$C_3$ alkyl, halo $C_1$-$C_3$ alkyl, $(CH_2)_{1-3}$OR$_6$, $C_3$-$C_6$ cycloalkyl, halo $C_3$-$C_6$ cycloalkyl, $C_1$-$C_3$ alkoxy, halo $C_1$-$C_3$ alkoxy, $C_1$-$C_3$ alkylthio, halo $C_1$-$C_3$ alkylthio, halogen, nitro, amino and cyano;

wherein, $R_6$ is selected from: H, —COR$_7$, —SO$_2$R$_8$ and —SiR$_9$R$_{10}$R$_{11}$;

wherein, $R_7$ is selected from $C_1$-$C_3$ alkyl and halo $C_1$-$C_3$ alkyl; $R_8$ is selected from $C_1$-$C_3$ alkyl, optionally substituted $C_1$-$C_3$ alkyl, $C_6$-$C_{10}$ aryl, and optionally substituted $C_6$-$C_{10}$ aryl; $R_9$, $R_{10}$ and $R_{11}$ are independently selected from $C_1$-$C_6$ alkyl.

In one embodiment, the invention relates to a compound of Formula (I), wherein $R_2$ is selected from H, $C_1$-$C_3$ alkyl, halo $C_1$-$C_3$ alkyl, $(CH_2)_{1-3}$OR$_6$, $C_3$-$C_6$ cycloalkyl, halo $C_3$-$C_6$ cycloalkyl, $C_1$-$C_3$ alkoxy, halo $C_1$-$C_3$ alkoxy, $C_1$-$C_3$ alkylthio, halo $C_1$-$C_3$ alkylthio, halogen, nitro, amino and cyano;

wherein, $R_6$ is selected from: H, —COR$_7$, —SO$_2$R$_8$ and —SiR$_9$R$_{10}$R$_{11}$;

wherein, $R_7$ is selected from —CH$_3$, $R_8$ is selected from —CF$_3$ and p-methyl phenyl; $R_9$, $R_{10}$ and $R_{11}$ are independently selected from methyl and tert-butyl.

In one embodiment, the invention relates to a compound of Formula (I), wherein $R_2$ is selected from H, $C_1$-$C_3$ alkyl, halo $C_1$-$C_3$ alkyl, $(CH_2)_{1-3}$OR$_6$, halogen, nitro, amino and cyano;

wherein, $R_6$ is selected from H, —COR$_7$, —SO$_2$R$_8$ and —SiR$_9$R$_{10}$R$_{11}$;

wherein, $R_7$ is selected from $C_1$-$C_6$ alkyl and halo $C_1$-$C_6$ alkyl; $R_8$ is selected from $C_1$-$C_6$ alkyl, optionally substituted $C_1$-$C_6$ alkyl, $C_6$-$C_{10}$ aryl, and optionally substituted $C_6$-$C_{10}$ aryl; $R_9$, $R_{10}$ and $R_{11}$ are independently selected from $C_1$-$C_6$ alkyl.

In one embodiment, the invention relates to a compound of Formula (I), wherein $R_2$ is selected from H, $C_1$-$C_3$ alkyl, halo $C_1$-$C_3$ alkyl, $(CH_2)_{1-3}$OR$_6$, halogen, nitro, amino and cyano;

wherein, $R_6$ is selected from: H, —COR$_7$, —SO$_2$R$_8$ and —SiR$_9$R$_{10}$R$_{11}$;

wherein, $R_7$ is selected from $C_1$-$C_3$ alkyl, and halo $C_1$-$C_3$ alkyl; $R_8$ is selected from $C_1$-$C_3$ alkyl, optionally substituted $C_1$-$C_3$ alkyl, $C_6$-$C_{10}$ aryl, and optionally substituted $C_6$-$C_{10}$ aryl; $R_9$, $R_{10}$ and $R_{11}$ are independently selected from $C_1$-$C_6$ alkyl.

In one embodiment, the invention relates to a compound of Formula (I), wherein $R_2$ is selected from H, $C_1$-$C_3$ alkyl, halo $C_1$-$C_3$ alkyl, $(CH_2)_{1-3}$OR$_6$, halogen, nitro, amino and cyano;

wherein, $R_6$ is selected from: H, —COR$_7$, —SO$_2$R$_8$ and —SiR$_9$R$_{10}$R$_{11}$;

wherein, $R_7$ is selected from —CH$_3$, $R_8$ is selected from —CF$_3$ and p-methyl phenyl; $R_9$, $R_{10}$ and $R_{11}$ are independently selected from methyl and tert-butyl.

In one embodiment, the invention relates to a compound of Formula (I), wherein $R_2$ is selected from H, $C_1$-$C_3$ alkyl, and $(CH_2)_{1-3}$OR$_6$;

wherein, $R_6$ is selected from H, —COR$_7$, —SO$_2$R$_8$, and —SiR$_9$R$_{10}$R$_{11}$;

wherein, $R_7$ is selected from $C_1$-$C_6$ alkyl, and halo $C_1$-$C_6$ alkyl; $R_8$ is selected from $C_1$-$C_6$ alkyl, optionally substituted $C_1$-$C_6$ alkyl, $C_6$-$C_{10}$ aryl, and optionally substituted $C_6$-$C_{10}$ aryl; $R_9$, $R_{10}$, and $R_{11}$ are independently selected from $C_1$-$C_6$ alkyl.

In one embodiment, the invention relates to a compound of Formula (I), wherein $R_2$ is selected from H, $C_1$-$C_3$ alkyl and $(CH_2)_{1-3}OR_6$;

wherein, $R_6$ is selected from H, —$COR_7$, —$SO_2R_8$ and —$SiR_9R_{10}R_{11}$;

wherein, $R_7$ is selected from $C_1$-$C_3$ alkyl and halo $C_1$-$C_3$ alkyl; $R_8$ is selected from $C_1$-$C_3$ alkyl, optionally substituted $C_1$-$C_3$ alkyl, $C_6$-$C_{10}$ aryl, and optionally substituted $C_6$-$C_{10}$ aryl; $R_9$, $R_{10}$ and $R_{11}$ are independently selected from $C_1$-$C_6$ alkyl.

In one embodiment, the invention relates to a compound of Formula (I), wherein $R_2$ is selected from H, $C_1$-$C_3$ alkyl and $(CH_2)_{1-3}OR_6$;

wherein, $R_6$ is selected from H, —$COR_7$, —$SO_2R_8$ and —$SiR_9R_{10}R_{11}$;

wherein, $R_7$ is selected from —$CH_3$; $R_8$ is selected from —$CF_3$ and p-methyl phenyl; $R_9$, $R_{10}$ and $R_{11}$ are independently selected from methyl, and tert-butyl.

In one embodiment, the invention relates to a compound of Formula (I), wherein, $R_3$ is selected from H and $C_1$-$C_3$ alkyl.

In one embodiment, the invention relates to a compound of Formula (I), wherein, $R_3$ is $C_1$-$C_3$ alkyl.

In one embodiment, the invention relates to a compound of Formula (I), wherein $R_4$ and $R_5$ each are independently selected from: H, —$COR_7$, —$SO_2R_8$, and —$SiR_9R_{10}R_{11}$;

wherein, $R_7$ is selected from $C_1$-$C_3$ alkyl, and halo $C_1$-$C_3$ alkyl; $R_8$ is selected from $C_1$-$C_3$ alkyl, optionally substituted $C_1$-$C_3$ alkyl, $C_6$-$C_{10}$ aryl, and optionally substituted $C_6$-$C_{10}$ aryl; $R_9$, $R_{10}$ and $R_{11}$ are independently selected from $C_1$-$C_6$ alkyl.

In one embodiment, the invention relates to a compound of Formula (I), wherein $R_4$ and $R_5$ each are independently selected from: H, —$COR_7$, —$SO_2R_8$, and —$SiR_9R_{10}R_{11}$;

wherein, $R_7$ is selected from —$CH_3$; $R_8$ is selected from —$CF_3$, and p-methyl phenyl; $R_9$, $R_{10}$ and $R_{11}$ are independently selected from methyl, and tert-butyl.

In one embodiment, the invention relates to a compound of Formula (I), which is selected from:

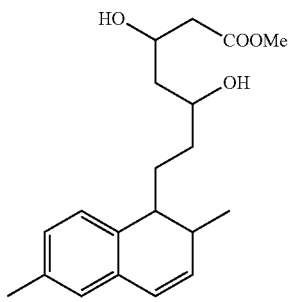

and diacetate, bis(4-methylbenzenesulfonate), bis(trifluoromethanesulfonate), and bis(tert-butyldimethylsilyl ether) thereof,

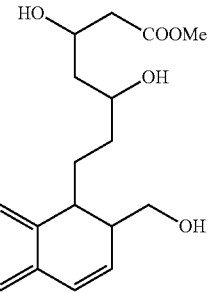

and triacetate, tris(4-methylbenzenesulfonate), tris (trifluoromethanesulfonate), and tris (tert-butyldimethylsilyl ether) thereof.

As used herein, the term "$C_1$-$C_6$ alkyl" refers to a linear or branched alkyl having 1-6 carbon atoms. Examples of $C_1$-$C_6$ alkyl include, but are not limited to methyl, ethyl, n-propyl, isopropyl, tert-butyl, n-pentyl and n-hexyl.

Similarly, the term "$C_1$-$C_3$ alkyl" refers to a linear or branched alkyl having 1-3 carbon atoms. Examples of $C_1$-$C_3$ alkyl include, but are not limited to methyl, ethyl, n-propyl, and isopropyl.

The term "$C_1$-$C_6$ alkoxy" refers to —O—$C_1$-$C_6$ alkyl.

The term "$C_1$-$C_6$ alkylthio" refers to —S—$C_1$-$C_6$ alkyl.

Similarly, "$C_1$-$C_3$ alkoxy" and "$C_1$-$C_3$ alkylthio" have similar meanings.

The term "$C_3$-$C_7$ cycloalkyl" refers to an alkyl having a saturated 3-7 membered monocyclic system, wherein $C_3$-$C_7$ cycloalkyl may be cyclopropyl, cyclobutyl, cyclopentyl, cyclohexyl, and cycloheptyl.

Similarly, the term "$C_3$-$C_6$ cycloalkyl" refers to an alkyl having a saturated 3-6 membered monocyclic system, wherein $C_3$-$C_6$ cycloalkyl may be cyclopropyl, cyclobutyl, cyclopentyl, and cyclohexyl.

The term "halogen" refers to F, Cl, Br or I.

The term "halo-XX group" refers to a halogenated XX group. For example, "halo $C_1$-$C_6$ alkyl" refers to halogenated —$C_1$-$C_6$ alkyl. The term "halo $C_3$-$C_7$ cycloalkyl" refers to halogenated —$C_3$-$C_7$ cycloalkyl. Similarly, the term halo $C_1$-$C_6$ alkylthio, halo $C_1$-$C_6$ alkoxy, halo $C_3$-$C_6$ cycloalkyl, halo $C_1$-$C_3$ alkoxy, halo $C_1$-$C_3$ alkylthio have similar meanings as described above.

The term "$C_6$-$C_{10}$ aryl" refers to a monovalent aromatic alkyl having 6-10 carbon atoms. Examples of aryl include, but are not limited to phenyl, tolyl, ethylphenyl, naphthyl, etc.

As used herein, the term "a pharmaceutically acceptable salt of the compound of Formula (I)" refers to an organic acid addition salt formed by a pharmaceutically acceptable anion (such as methylbenzenesulfonate radical, methanesulfonate radical, malate radical, acetate radical, citrate radical, malonate radical, tartrate radical, succinate radical, benzoate radical, ascorbate radical, α-ketoglutarate radical, and α-glycerophosphate) of an organic acid. It may also form a suitable inorganic salt, including, but not limited to hydrochlorate, sulfate, nitrate, bicarbonate and carbonate, phosphate, hydrobromate, hydriodate, etc.

A pharmaceutically acceptable salt can be obtained by the standard processes well known in the art, for example, by reacting a sufficient amount of an alkaline compound with a suitable acid providing a pharmaceutically acceptable anion.

*Monascus*-fermented rice or extract thereof according to the invention may be the commercially available *Monascus*-fermented rice (*Monascus*-fermented rice dry powder, fermentation products of *Monascus*-fermented rice, red kojic rice), or extract of *Monascus*-fermented rice (such as Xuezhikang capsule, Xuezhikang tablet or raw material thereof).

The extract of *Monascus*-fermented rice according to the invention may be prepared by the following method (but not limited to the following method):

1) to 1 part of *Monascus*-fermented rice by weight, adding 2-10 parts of 50-100% (v/v) ethanol or methanol or methanol/ethanol aqueous solution, or ethyl acetate (or other organic solvent) by volume each time, heating the resultant mixture to reflux for 1-3 h, and performing the extraction for 2-3 times;

2) filtrating the extracting solution, combining the filtrate, and optionally recovering the solvent; and 3) concentrating the filtrate obtained in the step 2) to a thick paste.

As used herein, the term "solvate" may be formed by a common organic solvent: hydrocarbon solvent such as benzene or toluene; chlorinated solvent such as chloroform and dichloromethane; alcohol solvent such as methanol, ethanol or isopropanol; ether solvent such as diethyl ether or tetrahydrofuran, or ester solvent such as ethyl acetate. Alternatively, the solvate of the compound of Formula (I) may be formed by water, and in this case, it is a hydrate.

As used herein, the term "hydrate" refers to the compound or a salt thereof according to the invention further comprising a stoichiometric or non-stoichiometric water bound via a non-covalent intermolecular force.

As used herein, unless otherwise specified, the term "prodrug" refers to a derivative which can be hydrolyzed, oxidized or subjected to other reactions under biological conditions (in vitro or in vivo) to provide a compound according to the invention. A prodrug is only reacted in the reaction under biological conditions to form an active compound, or has activity in its unreacted form. In general, a prodrug can be prepared by well-known methods, for example, the methods described in Burger's Medicinal Chemistry and Drug Discovery (1995) 172-178, 949-982 (edited by Manfred E. Wolff, the 5$^{th}$ edition).

The stereochemical definitions and principles used herein generally follow McGraw-Hill Dictionary of Chemical Terms (S. P. Parker, Ed., McGraw-Hill Book Company, New York, 1984); and Eliel, E. and Wilen, S., Stereochemistry of Organic Compounds (John Wiley & Sons, Inc., New York, 1994). Many organic compounds are present in their optically active forms, i.e., have the ability of rotating the plane of polarization of linearly polarized light.

As used herein, the term "treatment" generally refers to the acquirement of a desired pharmacological and/or physiological effect. The effect may be preventive depending on complete or partial prevention of a disease or symptoms thereof; and/or may be therapeutic depending on partial or complete stabilization or cure of a disease or side effects caused by the disease. The "treatment" used herein covers any treatment of a disease in a patient, comprising: (a) preventing a disease or a symptom in a patient who is susceptible to the disease or the symptom but has not been diagnosed to suffer from the disease yet; (b) inhibiting the symptom of a disease, i.e., preventing the progress thereof; or (c) alleviating the symptom of a disease, i.e., resulting in degeneration of the disease or the symptom.

The compound of the invention can be prepared by conventional organochemical synthetic methods. For example, the invention relates to a method for preparing a compound of Formula (I):

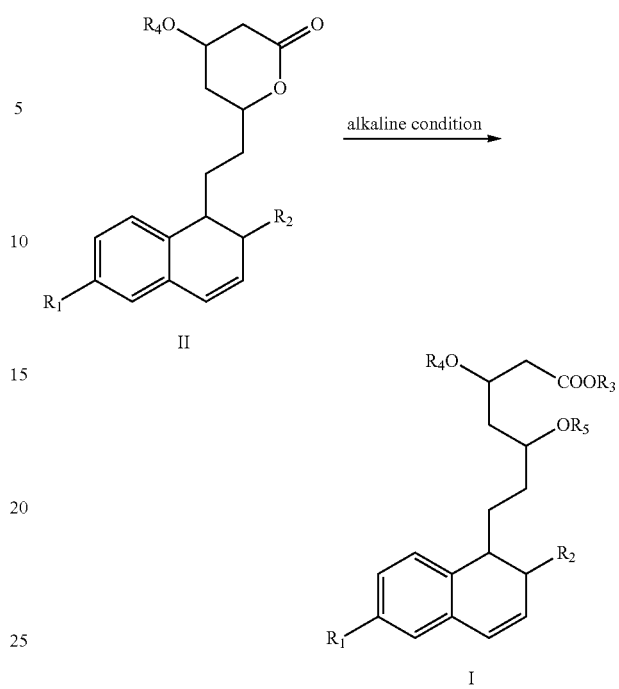

reacting a compound of Formula (II) under alkaline condition, or adding an esterification reagent under alkaline condition, to prepare the compound of Formula (I), wherein, in Formula (II), $R_1$, $R_2$ and $R_4$ have the same meanings as defined above in Formula (I).

The pH range of the alkaline condition is 7.5-14, and optionally, an alkaline reagent such as sodium hydroxide, potassium hydroxide, ammonia water and sodium carbonate, or a solvent may be added; the esterification reagent may be selected from lower alcohol such as methanol and ethanol; anhydride (acetic anhydride, sulfonic anhydride, trifluormethane sulfonic anhydride, etc.), acyl chloride (toluene sulfonyl chloride), and chlorosilane (tert-butyldimethylchlorosilane).

Conventional chemical conversion may be used to carry out the invention. A person skilled in the art can determine suitable chemical agents, solvents, protective groups and reaction conditions for use in the chemical conversions. Relevant information can be found in, for example, R. Larock, *Comprehensive Organic Transformations*, VCH publisher (1989); T. W. Greene and P. G. M. Wuts, *Protective Groups in Organic Synthesis*, the 3$^{rd}$ edition, John Wiley and Sons (1999); L. Fieser and M. Fieser, *Fieser and Fieser's Reagents for Organic Synthesis*, John Wiley and Sons (1994); and John Wiley and Sons, *Encyclopedia of Reagents for Organic Synthesis*, edited by L. Paquette (1995) and the later editions.

A protective group refers to a group which can prevent an active moiety (such as hydroxyl or amino) from being disturbed in the subsequent reactions upon conjugation to the active moiety, and can be removed by conventional methods after the reactions. Examples of hydroxyl protective groups include, but are not limited to, alkyl, phenylmethyl (benzyl), allyl, trityl (i.e., triphenylmethyl), acyl (such as, benzoyl, acetyl or HOOC—X"—CO—, X" is alkylidene group, alkenylene group, cycloalkylidene group or arylene group), silyl (e.g., trimethylsilyl, triethylsilyl and tert-butyldimethylsilyl), alkoxycarbonyl, aminocarbonyl (e.g., dimethylaminocarbonyl, methylethylaminocarbonyl and phenylaminocarbonyl), alkoxymethyl, phenylmethoxymethyl and alkylmercapto-methyl. Examples of amino protective groups include, but are not limited to, alkoxycarbonyl, alkanoyl, aryloxycarbonyl, aryl-substituted alkyl, etc. Hydroxyl and amino protective groups have been discussed in T. W. Greene and P. G. M. Wuts, Protective Groups in Organic Synthesis, the second edition, John Wiley and Sons (1991). Both hydroxyl and amino protective groups can be removed by conventional methods after the reaction.

Another object of the invention is to provide a method for separating a compound. In particular, another object of the invention is to provide a method for extracting Compound 5 from *Monascus*-fermented rice or extract thereof, the method comprising the following steps:

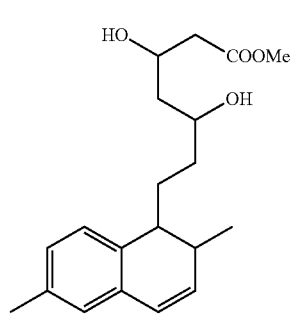 [SMILES: COC(=O)CC(O)CC(O)CCC1c2ccc(C)cc2C=CC1C]

Compound 5

1) extracting *Monascus*-fermented rice or extract thereof with ethyl acetate (or dichloromethane or methanol or ethanol, or methanol/ethanol aqueous solution) as a solvent;

2) separating the ethyl acetate (or dichloromethane or methanol or ethanol, or methanol/ethanol aqueous solution) extract obtained in Step 1) by silica gel column chromatography, and carrying out gradient elution with petroleum ether, ethyl acetate and methanol/ethanol, to obtain the ethyl acetate eluting fraction;

3) separating the ethyl acetate eluting fraction obtained in Step 2) by silica gel column chromatography, carrying out elution with dichloromethane-ethyl acetate-methanol, detecting and combining the fractions, to obtain 5 fractions in Step 3);

4) separating the second fraction obtained in Step 3) by C18 column chromatography, and carrying out gradient elution with acetonitrile-methanol-water, to obtain 82% (acetonitrile-methanol 1:1) aqueous solution eluting fraction;

5) further separating the 82% (acetonitrile-methanol 1:1) aqueous solution eluting fraction obtained in Step 4) by sephadex LH-20 column chromatography using dichloromethane-methanol as a mobile phase, analyzing and combining the fractions, to obtain 6 fractions in Step 5); and 6) purifying the third fraction obtained in Step 5) by chromatographic method using acetonitrile-methanol-water as a mobile phase and using C18 chromatographic column as a stationary phase, to obtain Compound 5.

In an embodiment, a method for extracting Compound 5 from *Monascus*-fermented rice or extract thereof, the method comprising the following steps:

1) extracting *Monascus*-fermented rice or extract thereof with 2-6-fold volume of ethyl acetate (or dichloromethane or methanol or ethanol, or methanol/ethanol aqueous solution) as a solvent for three times, 20-40 min for each time, combining the extracting solution, and concentrating it under reduced pressure to recover the solvent, and to obtain the ethyl acetate extract;

2) separating the ethyl acetate (or dichloromethane or methanol or ethanol, or methanol/ethanol aqueous solution) extract obtained in Step 1) by silica gel column chromatography, and carrying out gradient elution with petroleum ether, ethyl acetate and methanol or ethanol, to obtain the ethyl acetate eluting fraction;

3) separating the ethyl acetate eluting fraction obtained in Step 2) by silica gel column chromatography, carrying out elution with dichloromethane-ethyl acetate-methanol (30:30:1), analyzing and combining the fractions, to obtain 5 fractions in Step 3);

4) separating the second fraction obtained in Step 3) by C18 column chromatography, and carrying out gradient elution with 82% (acetonitrile-methanol 1:1) aqueous solution~100% (acetonitrile-methanol 1:1), to obtain 82% (acetonitrile-methanol 1:1) aqueous solution eluting fraction;

5) further separating the 82% (acetonitrile-methanol 1:1) aqueous solution eluting fraction obtained in Step 4) by sephadex LH-20 column chromatography using dichloromethane-methanol (2:1) as a mobile phase, analyzing and combining the fractions, to obtain 6 fractions in Step 5); and 6) purifying the third fraction obtained in Step 5) by chromatography using acetonitrile-methanol-water as a mobile phase and using C18 chromatographic column as a stationary phase, to obtain Compound 5

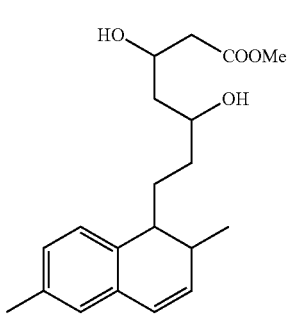

Compound 5

The invention further provides a pharmaceutical composition comprising the compound of Formula (I) according to the invention. The invention provides such a pharmaceutical composition, comprising at least one the compound of Formula (I) as described above, and optionally, a pharmaceutically acceptable excipient.

Methods for preparing a pharmaceutical composition comprising a certain amount of an active ingredient, are known or are obvious for a person skilled in the art according to the contents as disclosed in the invention. For example, as described in REMINGTON'S PHARMACEUTICAL SCIENCES, Martin, E. W., ed., Mack Publishing Company, 19th ed. (1995), methods for preparing a pharmaceutical composition comprising incorporating a suitable pharmaceutically acceptable excipient, carrier, diluent, etc.

The known methods for preparing a pharmaceutical preparation according to the invention include the conventional mixing, dissolving or freeze-drying methods. The compound according to the invention can be used to prepare a pharmaceutical composition, which is administered to a patient by various routes suitable for the selected administration mode, for example, oral, or parenteral route (intravenous, intramuscular, topical, or subcutaneous route).

Therefore, the compound of the invention in combination with a pharmaceutically acceptable carrier (such as an inert diluent or an assimilable edible carrier) can be administered systemically, e.g., orally. They can be encapsulated into a hard or soft shell gelatin capsule, and pressed into a table. For the treatment by oral administration, an active compound may be combined with one or more excipients, and be used in a form of a deglutible tablet, a buccal tablet, a troche, a capsule, an elixir, a suspension, a syrup, a wafer, etc. The composition and preparation shall comprise at least 0.1% of an active compound. The ratio of the composition to the preparation can be varied certainly, and the active compound may account for about 1 wt % to about 99 wt % of a given unit dosage form. In such a therapeutically active composition, the active compound is in an amount sufficient to obtain an effective dosage level.

A tablet, a troche, a pill, a capsule, and the like may include: a binder, such as tragacanth gum, arabic gum, maize starch or gelatin; an excipient, such as dicalcium phosphate; a disintegrant, such as maize starch, potato starch, and alginic acid etc; a lubricant, such as magnesium stearate; and a sweeting agent, such as sucrose, fructose, lactose or aspartame; or a flavoring agent, such as peppermint, winter green oil or cherry flavor. When the unit dosage form is a capsule, in addition to the above types of materials, it may comprise a liquid carrier, such as vegetable oil or polyethylene glycol. Various other materials may be present as a coating or change the physical form of a solid unit dosage form in other manners. For example, a tablet, a pill or a capsule may be coated with gelatin, wax, shellac or sugar etc. A syrup or elixir may comprise an active compound, sucrose or fructose as a sweeting agent, methyl p-hydroxybenzoate or propyl p-hydroxybenzoate as preservative, a dye and a flavoring agent (such as a cherry flavor or an orange flavor). Certainly, any material for preparing any unit dosage form should be pharmaceutically acceptable and be substantively not toxic in its applied amount. In addition, an active compound may be incorporated into a sustained release preparation and a sustained release device.

An active compound may also be administered intravenously or intraperitoneally by infusion or injection. An aqueous solution of an active compound or a salt thereof may be prepared, optionally, by mixing it with a non-toxic surfactant. A dispersing agent in glycerol, liquid polyethylene glycol, glycerin triacetate and a mixture thereof and in oil may also be prepared. Under the common conditions of storage and use, the preparations may comprise a preservative in order to suppress the growth of microbes.

A pharmaceutical dosage form suitable for injection or infusion may include a sterile aqueous solvent or a dispersing agent or a sterile powder comprising an active ingredient (optionally encapsulated into a liposome) of an immediate preparation such as a solution or a dispersing agent suitable for sterile injection or infusion. Under all the conditions, the final dosage form shall be sterile, liquid or stable under the production and storage conditions. A liquid carrier may be a solution or a liquid disperse medium, including, for example, water, ethanol, polyols (such as glycerol, propylene glycol, and liquid macrogol, etc), vegetable oil, a non-toxic glyceride and a suitable mixture thereof. A suitable fluidity may be retained, for example, by the formation of liposome, by retaining the desired particle size in the presence of a dispersing agent, or by using a surfactant. The effect of suppressing microbes can be obtained by various antibacterial agents and antifungal agents (such as paraben, chlorbutol, phenol, sorbic acid, and thiomersal, etc). In many conditions, an isotonizing agent, such as sugar, buffer or NaCl, is preferably comprised. By the use of a composition of delayed absorbents (e.g., aluminium monostearate and gelatin), an extended absorption of an injectable composition can be obtained.

A sterile injectable solution can be prepared by mixing a desired amount of an active compound in a suitable solvent with the desired various other ingredients as listed above, and then performing filtration and sterilization. In the case of a sterile powder for the preparation of a sterile injectable solution, the preferred preparation method is vacuum drying and freeze drying techniques, which will result in the production of the active ingredient and the powder of any other desired ingredient present in the previous sterile filtration solution.

A useful solid carrier includes crushed solid (such as talc, clay, microcrystalline cellulose, silicon dioxide, and aluminum oxide etc). A useful liquid carrier includes water, ethanol or ethylene glycol or water-ethanol/ethylene glycol mixture, in which the compound of the invention may be dissolved or dispersed in an effective amount, optionally, with the aid of a non-toxic surfactant. An adjuvant (such as a flavor) and an additional antimicrobial agent may be added to optimize the property for a given use.

A thickener (such as synthetic polymer, fatty acid, fatty acid salt and ester, fatty alcohol, modified cellulose or modified inorganic material) may also be used with a liquid carrier to form a coatable paste, gel, ointment, soap and the like, and be directly applied to the skin of a user.

A therapeutically effective amount of a compound or an active salt or derivative thereof not only depends on the specific salt selected, but also depends on the administration mode, the nature of the disease to be treated and the age and state of a patient, and finally depends on the decision made by an attending physician or a clinical physician.

Above preparation may be present in a unit dosage form, which is a physical dispersion unit comprising a unit dose, suitable for administration to a human body and other mammalian body. A unit dosage form may be capsule(s) or tablet(s). Depending on the particular treatment involved, the amount of an active ingredient in a unit dose may be varied or adjusted between about 0.1 and about 1000 mg or more.

The invention further provides use of the compound according to the invention or a pharmaceutical composition comprising the compound in the manufacture of a medicament, in particular a medicament for inhibiting HMG-CoA reductase. Correspondingly, the invention provides a method for preventing and/or treating dyslipidemia, hyperlipemia, or atherosclerosis in a patient, comprising administering a therapeutically effective amount of at least one compound of the invention to the patient in need of treatment. Dyslipidemia refers to a condition in which one or more blood lipid-associated indexes of human body do not fall into the corresponding normal ranges, including elevated total cholesterol, elevated low density lipoprotein cholesterol, elevated apolipoprotein B, elevated triglyceride, and the like. The invention provides a method for preventing and/or treating hypercholesterolemia, combined hyperlipidemia in a patient, comprising administering a therapeutically effective amount of at least one compound of the invention to the patient in need of treatment.

The invention provides a method for treating an increase in total cholesterol, an increase in low density lipoprotein cholesterol, an increase in apolipoprotein B, an increase in triglyceride and the like when the effect of a lifestyle intervention therapy (such as diet adjustment, body weight control, more exercise, and quitting smoking) is not satisfactory.

In above uses, the compound of the invention can be used alone, or in combination with an effective amount of additional lipid-regulatory drug(s). The additional lipid-regulatory drug includes cholesterol synthesis inhibitors (statins or salts thereof, such as lovastatin, pravastatin, simvastatin, fluvastatin, atorvastatin, and pitavastatin, etc), cholesterol absorption inhibitors (Ezetimibe and the like), fibrates (Lopid, lipanthyl ciprofibrate, bezafibrate, fenofibrate and gemfibrozil), nicotinic acids (nicotinic acid, inositol nicotinate, Dongzhiping, and niceritrol, etc), bile acid sequestrants, and phenoxy aromatic acids.

The compound according to the invention or a pharmaceutically acceptable salt thereof (such as acetate, malonate, tartrate, succinate, hydrochlorate, sulfate, and nitrate), may be used to prevent or treat above diseases.

In the following examples, the invention is explained more specifically. However, it should be understood that the following examples are provided for the purpose of illustrating the invention, rather than limiting the scope of the invention.

The chemical raw materials used in the following examples are either commercially available or prepared by the synthetic methods well known in the art.

EXAMPLE 1

The inventor further studied the ingredients of *Monascus*-fermented rice, and separated and purified a new statins compound (Compound 5).

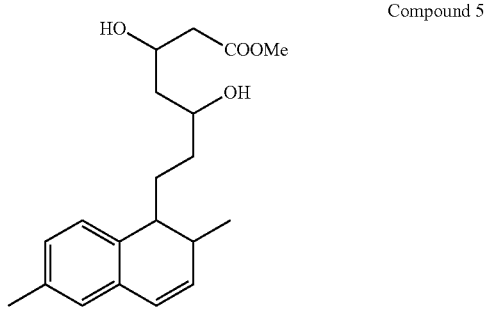

Compound 5

1. *Monascus*-fermented Rice 1) 6 kg *Monascus*-fermented rice dry powder (produced by WBL PEKING UNIVERSITY BIOTECH CO., LTD), was ultrasonically extracted with 2-6-fold volume of ethyl acetate (or dichloromethane or methanol or ethanol, or methanol/ethanol aqueous solution) as a solvent for three times, 20-40 min for each time, and the extracting solution was combined, and concentrated under reduced pressure to recover solvent, and obtain the ethyl acetate extract (240 g).

2) The ethyl acetate extract was separated by silica gel column chromatography, and gradient elution was carried out by using petroleum ether, ethyl acetate and methanol, to obtain the ethyl acetate eluting fraction (72 g).

3) The ethyl acetate eluting fraction was separated by silica gel column chromatography; dichloromethane-ethyl acetate-methanol (30:30:1) was used for elution; and 110 fractions were obtained, 10 ml for each fraction. After the tracking detection with TLC (or HPLC), the fractions having the same or similar chromatographic behavior were combined, and 5 fractions were obtained (i.e., the first 1-35; 36-50; 51-65; 66-89; 90-110 fractions were combined, respectively).

4) The second fraction (the combined first 36-50 fractions, 16 g) in Step 3) was separated by C18 column chromatography, and gradient elution was carried out by using 82% (acetonitrile-methanol 1:1) aqueous solution to 100% (acetonitrile-methanol 1:1), to obtain the 82% (acetonitrile-methanol 1:1) aqueous solution eluting fraction (3.2 g, collecting 900 ml in total).

5) The 82% (acetonitrile-methanol 1:1) aqueous solution eluting fraction was further separated by sephadex LH-20 column chromatography using dichloromethane-methanol 2:1 as a mobile phase, and 120 fractions in total were collected, 5 ml for each fraction. After the tracking detection with TLC (or HPLC), the fractions having the same or similar chromatographic behavior were combined, and 6 fractions were obtained (i.e., the first 1-40; 41-65; 66-80; 81-95; 96-110; 111-120 fractions were combined, respectively).

6) The third fraction (the combined first 66-80 fractions, 256 mg) in Step 5) was finally purified by semi-preparative high performance liquid chromatography, using 66% (acetonitrile-methanol 1:1) aqueous solution as a mobile phase, at a flow rate of 4 ml/min, and using C18 semi-preparative chromatographic column (10×250 mm, 5 μm) as a stationary phase, wherein the wavelength of DAD detector was 247 nm, and the fraction of the chromatographic peak at 22.8 min (21.5-23.5 min) was collected. After enrichment and concentration for several times, about 13 mg new compound (Compound 5) was obtained.

2. Xuezhikang 1) 3 kg of dry content powder of Xuezhikang capsule (WBL PEKING UNIVERSITY BIOTECH CO., LTD), was ultrasonically extracted with 2-6-fold volume of ethyl acetate (or dichloromethane or methanol) as a solvent for three times, 20-40 min for each time, and the extracting solution was combined, and concentrated under reduced pressure to recover the solvent, and to obtain the ethyl acetate extract (200 g).

2) The ethyl acetate extract was separated by silica gel column chromatography, and gradient elution was carried out by using petroleum ether, ethyl acetate and methanol, to obtain ethyl acetate eluting fraction (60 g).

3) The ethyl acetate eluting fraction was separated by silica gel column chromatography; dichloromethane-ethyl acetate-methanol (30:30:1) was used for elution; and 110 fractions were collected, 10 ml for each fraction. After the tracking detection with TLC (or HPLC), the fractions having the same or similar chromatographic behavior were combined, to obtain the 5 fractions (the first 1-35; 36-50; 51-65; 66-89; 90-110 fractions were combined, respectively) in Step 3).

4) The second fraction (the combined first 36-50 fractions, 14 g) in Step 3) was separated by C18 column chromatography, and gradient elution was carried out by using 82% (acetonitrile-methanol 1:1) aqueous solution~100% (acetonitrile-methanol 1:1), to obtain the 82% (acetonitrile-methanol 1:1) aqueous solution eluting fraction (2.8 g).

5) The 82% (acetonitrile-methanol 1:1) aqueous solution eluting fraction was further separated by sephadex LH-20 column chromatography using dichloromethane-methanol 2:1 as a mobile phase, and 120 fractions in total were collected, 5 ml for each fraction. After the tracking detection with TLC (or HPLC), the fractions having the same or similar chromatographic behavior were combined, and 6 fractions (i.e., the first 1-40; 41-65; 66-80; 81-95; 96-110; 111-120 fractions were combined, respectively) in Step 5) were obtained.

6) The third fraction (the combined first 66-80 fractions, 208 mg) in Step 5), was finally purified by semi-preparative high performance liquid chromatography, using 66% (acetonitrile-methanol 1:1) aqueous solution as a mobile phase, at a flow rate of 4 ml/min, and using C18 semi-preparative chromatographic column (10×250 mm, 5 μm) as a stationary phase, wherein the wavelength of DAD detector was 247 nm, and the fraction of the chromatographic peak at 22.8 min (21.5-23.5 min) was collected. After enrichment and concentration for several times, about 11.5 mg new compound (Compound 5) was obtained.

In the invention, other raw materials or preparations of *Monascus*-fermented rice may also be used as raw materials, such as Xuezhikang tablet (WBL PEKING UNIVERSITY BIOTECH CO., LTD).

EXAMPLE 2

Synthesis and Identification of Compound 5

Method A:

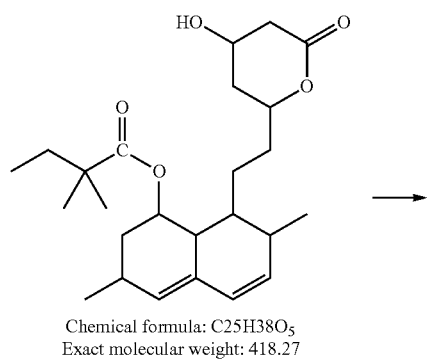

Chemical formula: C25H38O5
Exact molecular weight: 418.27

1

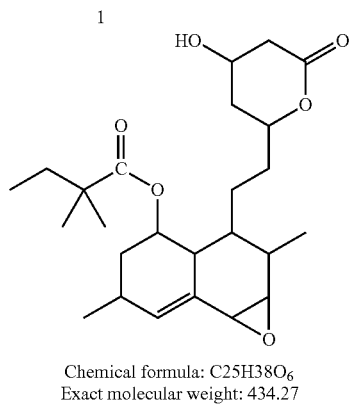

Chemical formula: C25H38O6
Exact molecular weight: 434.27

2

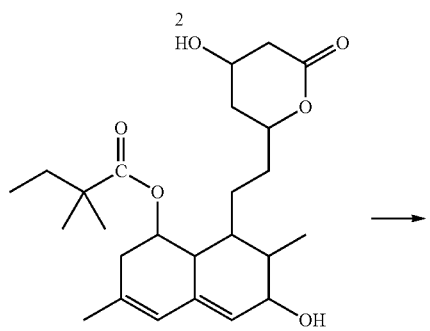

Chemical formula: C25H38O6
Exact molecular weight: 434.27

3

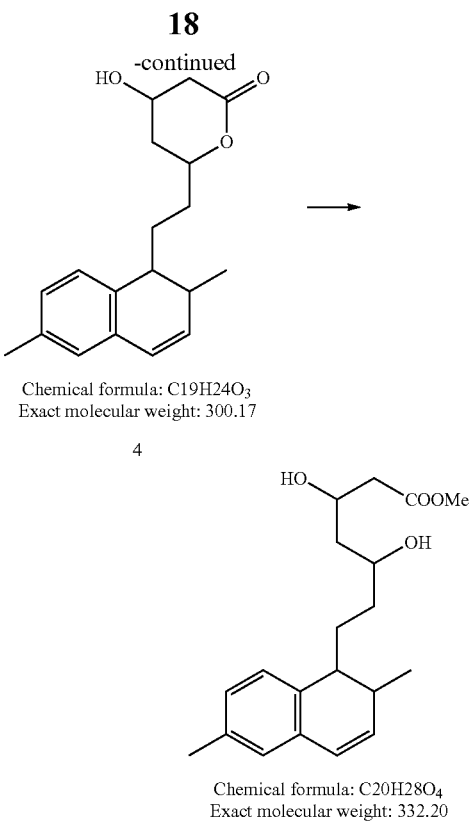

Chemical formula: C19H24O3
Exact molecular weight: 300.17

4

Chemical formula: C20H28O4
Exact molecular weight: 332.20

5

1. Synthesis of Compound 2

20.9 g (0.05 mol) of Compound 1 (Simvastatin, purchased from sigma) was dissolved in 500 ml dichloromethane, and 12 g (0.07 mol) of meta chloro perbenzoic acid was added. After stirring at room temperature for 40 min, the reaction was completed. Saturated sodium bicarbonate solution was added. After standing and delamination, the organic phase was washed sequentially with saturated sodium bicarbonate and saturated NaCl aqueous solution, dried and concentrated, and used in the next reaction without further separation.

2. Synthesis of Compound 3

To 250 ml of tetrahydrofuran, 0.085 mol of diethyl amine and 0.075 mol of tert-butyl alcohol were added. Under stirring in an ice bath, 0.15 mmol n-butyl lithium was added. After stirring for 20 min, the synthesized mixture in the above step was added in the reaction, and reacted under stirring in an ice bath. TLC was used to monitor the reaction. After the reaction was completed, the reaction was washed sequentially with water and saturated NaCl aqueous solution, and the organic phase was dried with anhydrous sodium sulfate, and concentrated. The resultant mixture was separated by column chromatography, to obtain 4.36 g of Compound 3, with a yield of 21%.

3. Synthesis of Compound 4

13 g of Compound 3 (0.03 mol) was dissolved in 60 ml chloroform, and the pH of the solution was adjusted to be acidic with hydrochloric acid. After stirring at room temperature overnight, the resultant mixture was washed sequentially with 10% sodium thiosulfate, water, and saturated NaCl aqueous solution. The organic solvent was removed under reduced pressure to obtain the crude product. After separation by column chromatography, 5.96 g of Compound 4 was obtained, with a yield of 62%.

4. Synthesis of Compound 5

Under the protection of $N_2$ gas, 7 g of Compound 4 was dissolved in 150 ml of methanol, and 0.3 mol of tetrabutylammonium hydrogen sulfate was added. The reaction was carried out under stirring and heating. TLC was used to monitor the reaction. After the reaction was completed, the solvent was removed under reduced pressure, and the residue was dissolved in 150 ml of mixed solution (water:heptane=1:1). After stirring for 2 h, the organic phase was separated, dried with anhydrous sodium sulfate, filtrated, and concentrated to obtain 6.82 g of Compound 5 of interest, with a yield of 88%.

Alternatively Method B:

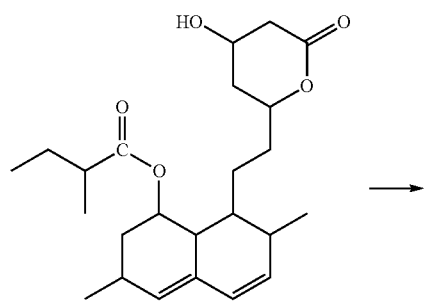

Chemical formula: $C_{24}H_{36}O_5$
Exact molecular weight: 404.26

1b

Chemical formula: $C_{24}H_{36}O_6$
Exact molecular weight: 420.25

2b

Chemical formula: $C_{24}H_{36}O_6$
Exact molecular weight: 420.25

3b

Chemical formula: $C_{19}H_{24}O_3$
Exact molecular weight: 300.17

4

Chemical formula: $C_{20}H_{28}O_4$
Exact molecular weight: 332.20

5

1. Synthesis of Compound 2b 20.2 g (0.05 mol) of Compound 1 (lovastatin, purchased from sigma) was dissolved in 500 ml of dichloromethane, and 12 g (0.07 mol) of meta chloro perbenzoic acid was added. The resultant mixture was stirred at room temperature for 40 min. After the reaction was completed, saturated sodium bicarbonate solution was added. After standing and delamination, the organic phase was washed sequentially with saturated sodium bicarbonate and saturated NaCl aqueous solution, dried and concentrated, and used in the next reaction without separation.

2. Synthesis of Compound 3b

To 250 ml of tetrahydrofuran, 0.085 mol of diethyl amine and 0.075 mol of tert-butyl alcohol were added. Under stirring in an ice bath, 0.15 mmol of n-butyl lithium was added. After stirring for 20 min, the mixture synthesized in the above step was added in the reaction, and reacted under stirring in an ice bath. TLC was used to monitor the reaction. After the reaction was completed, the reaction was washed sequentially with water and saturated NaCl aqueous solution, and the organic phase was dried with anhydrous sodium sulfate, and concentrated. The resultant mixture was separated by column chromatography, to obtain 4.22 g of Compound 3b, with a yield of 21%.

3. Synthesis of Compound 4

12.6 g of Compound 3b (0.03 mol) was dissolved in 60 ml chloroform, and the pH of the solution was adjusted to be acidic with hydrochloric acid. After stirring at room temperature overnight, the resultant mixture was washed sequentially with 10% sodium thiosulfate, water, and saturated NaCl aqueous solution. The organic solvent was removed under reduced pressure to obtain the crude product. After separation by column chromatography, 5.96 g of Compound 4 was obtained, with a yield of 62%.

4. Synthesis of Compound 5

Under the protection of $N_2$ gas, 7 g of Compound 4 was dissolved in 150 ml of methanol, and 0.3 mol of tetrabutylammonium hydrogen sulfate was added. The reaction was carried out under stirring and heating. TLC was used to monitor the reaction. After the reaction was completed, the solvent was removed under reduced pressure, and the residue was dissolved in 150 ml of mixed solution (water:heptane=1:1). After stirring for 2 h, the organic phase was separated, dried with anhydrous sodium sulfate, filtrated, and concentrated to obtain 6.82 g of Compound 5 of interest, with a yield of 88%.

Method for identifying the structure of Compound 5 was as follows:

1. Physical-chemical Data of the Compound

Light Yellow Oil.

The three maximum absorption peaks in UV spectrum: $\lambda_{max}(CH_2Cl_2)$=226.8 nm, 265.4 nm, and 301.2 nm, respectively.

FT-IR (KBr, cm$^{-1}$) spectrum: 3422 (—OH), 3013, 2952 (hydrogen on saturated carbon), 1732 (carbonyl).

HR-ESI-MS: m/z 355.1886 [M+Na]$^+$ (the calculated value was 355.1885, $C_{20}H_{28}O_4Na$).

2. Identification of its Formula

It could be found by analysis of the carbon spectrum of the compound ($^{13}$C-NMR and DEPT) that the compound included 20 carbon atoms, which were 3 methyl groups (1 of which was methoxy, and 1 of which was linked to sp$^2$ carbon), 4 methylene groups, 9 methyne groups (5 of which were sp$^2$ carbons), and 4 quaternary carbon atoms (1 of which was the carbon atom of carbonyl), and it could also be found that there were 8 carbon atoms (δ 126.9, 126.9, 127.2, 127.5, 133.4, 134.6, 135.9, 136.1) in the olefinic carbon region. It could be deduced from $^1$H-$^1$H COSY correlated spectrum (FIG. 1A) that the bold line represents the C2'-C4 fragment and the C7-C8 fragment. It could be deduced from the 8 carbon atoms in the olefinic carbon region that the compound had 4 C=C bonds. It could be found by further analysis of HMBC correlated signal that there were correlated signals between 6-Me and C5, C7; between H-5 and C6, C7; between H-4 and C5, C8a; between H-3 and C4a; between H-1 and C8a, C4a; between H-8 and C8a, C4a, and the like, and therefore, it could be deduced that the compound has a statin nuclear structure of 1, 2-dihydronaphthalene ring moiety. It could also be found from HMBC spectrum (FIG. 1AB) that there were correlated signals between the methyl of methoxy (δ 3.69), H-2'(δ 2.46/2.48) & H-3'(δ 2.45) and C1'(δ 173.0), indicating that methoxy was linked to C1'. Therefore, it could be deduced that the compound was a methyl-esterified statin derivative. Further based on the HR-ESI-MS result, it was deduced that the compound was: methyl 7-(2,6-dimethyl-1,2-dihydronaphthalen-1-yl)-3,5-dihydroxyheptanoate. The formula was shown in FIG. 1.

3. NMR Data on Compound 5

TABLE 1

| | NMR data on Compound 5 (600 MHz, CDCl$_3$, δ is expressed as ppm, J is expressed as Hz) | | | |
|---|---|---|---|---|
| Position | $^{13}$C-NMR | $^1$H-NMR | $^1$H-$^1$H COSY | HMBC (H→C) |
| 1 | 42.2 | 2.57 (1H, m) | 7'a, 7'b, 2 | 7', 2, 4a, 8a |
| 2 | 32.7 | 2.68 (1H, m) | 2-Me, 3 | 1 |
| 3 | 134.6 | 5.76 (1H, dd, 9.6, 3.0) | 4, 2 | 4a |
| 4 | 126.9 | 6.35 (1H, dd, 9.6, 2.4) | 3 | 8a, 5 |

TABLE 1-continued

| | NMR data on Compound 5 (600 MHz, CDCl$_3$, δ is expressed as ppm, J is expressed as Hz) | | | |
|---|---|---|---|---|
| Position | $^{13}$C-NMR | $^1$H-NMR | $^1$H-$^1$H COSY | HMBC (H→C) |
| 4a | 133.4 | — | — | — |
| 5 | 126.9 | 6.85 (1H, s) | — | 6, 7 |
| 6 | 136.1 | — | — | — |
| 7 | 127.2 | 6.93 (1H, d, 7.8) | 8 | 5, 8 |
| 8 | 127.5 | 6.99 (1H, d, 7.8) | 7 | 7, 4a, 8a |
| 8a | 135.9 | — | — | |
| 1' | 173.0 | — | | |
| 2' | 41.7 | 2.46 (1H, m) a | 3' | 4', 3', 1' |
| | | 2.48 (1H, m) b | | |
| 3' | 69.2 | 2.45 (1H, m) | 2'a, 2'b, 4' | 1', 4' |
| 4' | 42.4 | 1.51 (1H, m) a | 5', 3' | 6', 2', 3', 5' |
| | | 1.52 (1H, m) b | | |
| 5' | 72.9 | 3.76 (1H, m) | 4'a, 4'b | 3' |
| 6' | 36.0 | 1.31 (1H, m) a | 7'a, 7'b, 5' | 1, 5' |
| | | 1.45 (1H, m) b | | |
| 7' | 22.9 | 1.57 (1H, m) a | 1, 6'a, 6'b | 8a, 2, 6', 1, 5' |
| | | 1.66 (1H, m) b | | |
| 2-Me | 15.0 | 1.03 (3H, d, 7.2) | 2 | 1, 2, 3 |
| 6-Me | 21.1 | 2.29 (3H, s) | — | 6, 5, 7 |
| 1'-OMe | 51.9 | 3.69 (3H, s) | — | 1' |

EXAMPLE 3

Synthesis of Compound 5a

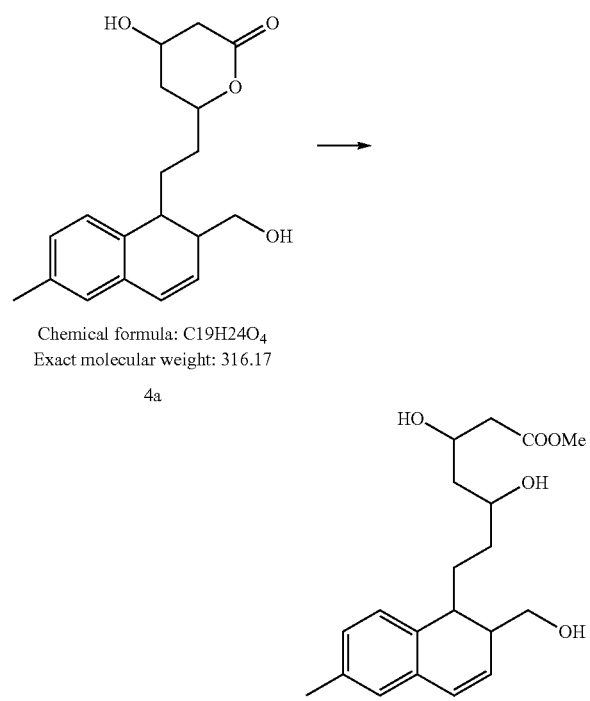

Chemical formula: C19H24O4
Exact molecular weight: 316.17

4a

Chemical formula: C20H28O5
Exact molecular weight: 348.19

5a

1. Synthesis of Compound 5a

Under the protection of $N_2$ gas, 7.4 g of Compound 4a was dissolved in 150 ml of methanol, and 0.3 mol of tetrabutylammonium hydrogen sulfate was added. The reaction was carried out under stirring and heating. TLC was used to monitor the reaction. After the reaction was completed, the solvent was removed under reduced pressure, and the residue was dissolved in 150 ml of mixed solution (water:heptane=1:1). After stirring for 2 h, the organic phase was separated, dried with anhydrous sodium sulfate, filtrated, and concentrated to obtain 6.91 g of Compound 5a of interest, with a yield of 85%.

EXAMPLE 4

Assay on HMG-CoA Reductase-Inhibiting Activity

1. Experimental Materials 1.1 Drugs

Compound 5—prepared by the inventor

Lovastatin standard substance—purchased from Sigma Company 1.2 Enzyme

Rat liver microsomes (HMG-CoA reductase) were commercially purchased, or were prepared by reference to the following method: the male rat liver was removed and rinsed with KESD buffer, and then centrifuged at 12,000 g for 15 min. The supernatant was taken. After centrifugation at 105,000 g for 90 min twice, the centrifuged pellets resulted from centrifugation were collected. To the centrifuged pellets, 8.3% glycerol was added, and the resultant mixture was heated in a 37° C. warm bath for 1 h. The crude product of the rat liver microsomes was purified with saturated ammonium sulfate, and the 35-50% purified fraction was collected. The rat liver microsomes obtained were stored in −80° C. refrigerator.

1.3 Reagents

Potassium chloride, potassium dihydrogen phosphate, ethylenediamine tetra acetic acid, dithiothreitol—purchased from Beijing Chemical Reagent Company nicotinamide-adenine dinucleotide phosphate (NADPH)—purchased from Merck Company 3-hydroxy-3-methylglutaryl-coenzyme A (HMG-CoA)—purchased from Sigma Company 2. Experimental Method Compound 5 was dissolved in 75% ethanol solution, at an initial concentration of 8.6 mg/ml, and was subjected to stepwise dilution to obtain 4.3 mg/ml, 2.15 mg/ml. The total volume of the test system was 250 μl, and the concentrations of various ingredients were as follows: 200 mM potassium chloride, 160 mM potassium dihydrogen phosphate, 4 mM ethylenediamine tetra acetic acid, 10 mM dithiothreitol, and the concentrations for the two substrates nicotinamide adenine dinucleotide and 3-hydroxy-3-methylglutaryl-coenzyme A were 200 μM and 50 μM, pH 6.8, respectively, wherein 30 μl was added for enzyme, 5 μl was added for the test group, and 5 μl (solvent for dissolving the sample) was added for the control group. The dynamic change in $OD_{340}$ was determined at 37° C. by Versamax ELISA Microplate Reader. The decreasing rate of $OD_{340}$ (represented by slope) was measured within 5 min, to evaluate the HMG-CoA reductase activity, and to further evaluate the enzyme-inhibiting activity. The results were shown in Table 2.

3. Experiment Results

The experimental results show that Compound 5 inhibited the HMG-CoA reductase activity, and exhibited a dose-response relationship, indicating that the compound had a good inhibitory effect on the HMG-CoA reductase activity.

TABLE 2

The detection results on activity of enzyme inhibitors

| Sample name | Concentration of the inhibitor (mg/ml) | Volume of the inhibitor (μl) | Final concentration (μg/ml) | Slope | Inhibition rate (%) |
|---|---|---|---|---|---|
| blank control | — | — | — | 13.5 | — |
| lovastatin | 4.0 | 5 | 80 | 8.2 | 39.2 |
| Compound 5 | 8.6 | 5 | 172 | 7.8 | 42.2 |
|  | 4.3 | 5 | 86 | 9.0 | 33.3 |
|  | 2.15 | 5 | 43 | 10.9 | 19.2 |

* blank control is a solvent
Lovastatin is a positive control.

The invention claimed is:

1. A compound of Formula (I), or a stereoisomer, tautomer, racemate, or pharmaceutically acceptable salt thereof:

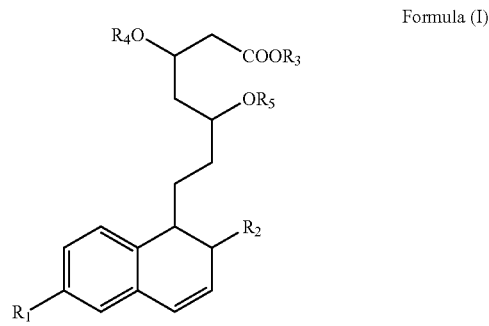

Formula (I)

$R_1$ is selected from H, $C_1$-$C_6$ alkyl, halo $C_1$-$C_6$ alkyl, $(CH_2)_{1-6}OH$, $C_3$-$C_7$ cycloalkyl, halo $C_3$-$C_7$ cycloalkyl, $C_1$-$C_6$ alkoxy, halo $C_1$-$C_6$ alkoxy, $C_1$-$C_6$ alkylthio, halo $C_1$-$C_6$ alkylthio, halogen, nitro, amino and cyano;

$R_2$ is selected from H, $C_1$-$C_6$ alkyl, halo $C_1$-$C_6$ alkyl, $(CH_2)_{1-6}OR_6$, $C_3$-$C_7$ cycloalkyl, halo $C_3$-$C_7$ cycloalkyl, $C_1$-$C_6$ alkoxy, halo $C_1$-$C_6$ alkoxy, $C_1$-$C_6$ alkylthio, halo $C_1$-$C_6$ alkylthio, halogen, nitro, amino and cyano;

$R_3$ is selected from H, $C_1$-$C_6$ alkyl;

$R_4$ and $R_5$ each are independently selected from: H, —$COR_7$, —$SO_2R_8$, and —$SiR_9R_{10}R_{11}$;

wherein, $R_7$ is selected from $C_1$-$C_6$ alkyl and halo $C_1$-$C_6$ alkyl; $R_8$ is selected from $C_1$-$C_6$ alkyl, optionally substituted $C_1$-$C_6$ alkyl, $C_6$-$C_{10}$ aryl, and optionally substituted $C_6$-$C_{10}$ aryl; $R_9$, $R_{10}$ and $R_{11}$ are independently selected from $C_1$-$C_6$ alkyl;

wherein, $R_6$ has the same definition as $R_4$ and $R_5$;

wherein, the following compounds are excluded;

the compound of Formula (I) wherein $R_1$ is $(CH_2)OH$, $R_2$ is methyl, and $R_3$, $R_4$ and $R_5$ are H, and the compound of Formula (I) wherein $R_1$, $R_3$, $R_4$ and $R_5$ are H and $R_2$ is methyl.

2. The compound according to claim 1, wherein, $R_1$ is selected from H, $C_1$-$C_3$ alkyl, halo $C_1$-$C_3$ alkyl, $(CH_2)_{1-3}OH$, $C_3$-$C_6$ cycloalkyl, halo $C_3$-$C_6$ cycloalkyl, $C_1$-$C_3$ alkoxy, halo $C_1$-$C_3$ alkoxy, $C_1$-$C_3$ alkylthio, halo $C_1$-$C_3$ alkylthio, halogen, nitro, amino and cyano.

3. The compound according to claim 1, wherein, $R_1$ is selected from H, $C_1$-$C_3$ alkyl, halo $C_1$-$C_3$ alkyl, $(CH_2)_{1-3}OH$, halogen, nitro, amino and cyano.

4. The compound according to claim 1, wherein $R_1$ is selected from H, $C_1$-$C_3$ alkyl, and $(CH_2)_{1-3}OH$.

5. The compound according to claim 1, wherein
R$_2$ is selected from H, C$_1$-C$_3$ alkyl, halo C$_1$-C$_3$ alkyl, (CH$_2$)$_{1-3}$OR$_6$, C$_3$-C$_6$ cycloalkyl, halo C$_3$-C$_6$ cycloalkyl, C$_1$-C$_3$ alkoxy, halo C$_1$-C$_3$ alkoxy, C$_1$-C$_3$ alkylthio, halo C$_1$-C$_3$ alkylthio, halogen, nitro, amino and cyano;
wherein, R$_6$ is selected from H, —COR$_7$, —SO$_2$R$_8$, and —SiR$_9$R$_{10}$R$_{11}$;
wherein, R$_7$ is selected from C$_1$-C$_6$ alkyl, and halo C$_1$-C$_6$ alkyl; R$_8$ is selected from C$_1$-C$_6$ alkyl, optionally substituted C$_1$-C$_6$ alkyl, C$_6$-C$_{10}$ aryl, and optionally substituted C$_6$-C$_{10}$ aryl; R$_9$, R$_{10}$ and R$_{11}$ are independently selected from C$_1$-C$_6$ alkyl.

6. The compound according to claim 1, wherein
R$_2$ is selected from H, C$_1$-C$_3$ alkyl, halo C$_1$-C$_3$ alkyl, (CH$_2$)$_{1-3}$OR$_6$, C$_3$-C$_6$ cycloalkyl, halo C$_3$-C$_6$ cycloalkyl, C$_1$-C$_3$ alkoxy, halo C$_1$-C$_3$ alkoxy, C$_1$-C$_3$ alkylthio, halo C$_1$-C$_3$ alkylthio, halogen, nitro, amino and cyano;
wherein, R$_6$ is selected from: H, —COR$_7$, —SO$_2$R$_8$, and —SiR$_9$R$_{10}$R$_{11}$;
wherein, R$_7$ is selected from C$_1$-C$_3$ alkyl, and halo C$_1$-C$_3$ alkyl; R$_8$ is selected from C$_1$-C$_3$ alkyl, optionally substituted C$_1$-C$_3$ alkyl, C$_6$-C$_{10}$ aryl, and optionally substituted C$_6$-C$_{10}$ aryl; R$_9$, R$_{10}$ and R$_{11}$ are independently selected from C$_1$-C$_6$ alkyl.

7. The compound according to claim 1, wherein
R$_2$ is selected from H, C$_1$-C$_3$ alkyl, halo C$_1$-C$_3$ alkyl, (CH$_2$)$_{1-3}$OR$_6$, C$_3$-C$_6$ cycloalkyl, halo C$_3$-C$_6$ cycloalkyl, C$_1$-C$_3$ alkoxy, halo C$_1$-C$_3$ alkoxy, C$_1$-C$_3$ alkylthio, halo C$_1$-C$_3$ alkylthio, halogen, nitro, amino and cyano;
wherein, R$_6$ is selected from: H, —COR$_7$, —SO$_2$R$_8$, and —SiR$_9$R$_{10}$R$_{11}$;
wherein, R$_7$ is selected from —CH$_3$; R$_8$ is selected from —CF$_3$ and p-methylphenyl; R$_9$, R$_{10}$ and R$_{11}$ are independently selected from methyl and tert-butyl.

8. The compound according to claim 1, wherein
R$_2$ is selected from H, C$_1$-C$_3$ alkyl, halo C$_1$-C$_3$ alkyl, (CH$_2$)$_{1-3}$OR$_6$, halogen, nitro, amino and cyano;
wherein, R$_6$ is selected from H, —COR$_7$, —SO$_2$R$_8$, and —SiR$_9$R$_{10}$R$_{11}$;
wherein, R$_7$ is selected from C$_1$-C$_6$ alkyl, and halo C$_1$-C$_6$ alkyl; R$_8$ is selected from C$_1$-C$_6$ alkyl, optionally substituted C$_1$-C$_6$ alkyl, C$_6$-C$_{10}$ aryl, and optionally substituted C$_6$-C$_{10}$ aryl; R$_9$, R$_{10}$ and R$_{11}$ are independently selected from C$_1$-C$_6$ alkyl.

9. The compound according to claim 1, wherein
R$_2$ is selected from H, C$_1$-C$_3$ alkyl, halo C$_1$-C$_3$ alkyl, (CH$_2$)$_{1-3}$OR$_6$, halogen, nitro, amino and cyano;
wherein, R$_6$ is selected from: H, —COR$_7$, —SO$_2$R$_8$, and —SiR$_9$R$_{10}$R$_{11}$;
wherein, R$_7$ is selected from C$_1$-C$_3$ alkyl and halo C$_1$-C$_3$ alkyl; R$_8$ is selected from C$_1$-C$_3$ alkyl, optionally substituted C$_1$-C$_3$ alkyl, C$_6$-C$_{10}$ aryl, and optionally substituted C$_6$-C$_{10}$ aryl; R$_9$, R$_{10}$ and R$_{11}$ are independently selected from C$_1$-C$_6$ alkyl.

10. The compound according to claim 1, wherein
R$_2$ is selected from H, C$_1$-C$_3$ alkyl, halo C$_1$-C$_3$ alkyl, (CH$_2$)$_{1-3}$OR$_6$, halogen, nitro, amino and cyano;
wherein, R$_6$ is selected from: H, —COR$_7$, —SO$_2$R$_8$ and —SiR$_9$R$_{10}$R$_{11}$;
wherein, R$_7$ is selected from —CH$_3$; R$_8$ is selected from —CF$_3$ and p-methyl phenyl; R$_9$, R$_{10}$ and R$_{11}$ are independently selected from methyl and tert-butyl.

11. The compound according to claim 1, wherein
R$_2$ is selected from H, C$_1$-C$_3$ alkyl and (CH$_2$)$_{1-3}$OR$_6$;
wherein, R$_6$ is selected from H, —COR$_7$, —SO$_2$R$_8$ and —SiR$_9$R$_{10}$R$_{11}$;
wherein, R$_7$ is selected from C$_1$-C$_6$ alkyl and halo C$_1$-C$_6$ alkyl; R$_8$ is selected from C$_1$-C$_6$ alkyl, optionally substituted C$_1$-C$_6$ alkyl, C$_6$-C$_{10}$ aryl, and optionally substituted C$_6$-C$_{10}$ aryl; R$_9$, R$_{10}$ and R$_{11}$ are independently selected from C$_1$-C$_6$ alkyl.

12. The compound according to claim 1, wherein
R$_2$ is selected from H, C$_1$-C$_3$ alkyl, and (CH$_2$)$_{1-3}$OR$_6$;
wherein, R$_6$ is selected from H, —COR$_7$, —SO$_2$R$_8$, and —SiR$_9$R$_{10}$R$_{11}$;
wherein, R$_7$ is selected from C$_1$-C$_3$ alkyl and halo C$_1$-C$_3$ alkyl; R$_8$ is selected from C$_1$-C$_3$ alkyl, optionally substituted C$_1$-C$_3$ alkyl, C$_6$-C$_{10}$ aryl, and optionally substituted C$_6$-C$_{10}$ aryl; R$_9$, R$_{10}$ and R$_{11}$ are independently selected from C$_1$-C$_6$ alkyl.

13. The compound according to claim 1, wherein
R$_2$ is selected from H, C$_1$-C$_3$ alkyl, and (CH$_2$)$_{1-3}$OR$_6$;
wherein, R$_6$ is selected from H, —COR$_7$, —SO$_2$R$_8$, and —SiR$_9$R$_{10}$R$_{11}$;
wherein, R$_7$ is selected from —CH$_3$; R$_8$ is selected from —CF$_3$ and p-methyl phenyl; R$_9$, R$_{10}$ and R$_{11}$ are independently selected from methyl and tert-butyl.

14. The compound according to claim 1, wherein
R$_3$ is selected from H and C$_1$-C$_3$ alkyl.

15. The compound according to claim 1, wherein
R$_3$ is C$_1$-C$_3$ alkyl.

16. The compound according to claim 1, wherein
R$_4$ and R$_5$ each are independently selected from: H, —COR$_7$, —SO$_2$R$_8$, and —SiR$_9$R$_{10}$R$_{11}$;
wherein, R$_7$ is selected from C$_1$-C$_3$ alkyl, and halo C$_1$-C$_3$ alkyl; R$_8$ is selected from C$_1$-C$_3$ alkyl, optionally substituted C$_1$-C$_3$ alkyl, C$_6$-C$_{10}$ aryl, and optionally substituted C$_6$-C$_{10}$ aryl; R$_9$, R$_{10}$ and R$_{11}$ are independently selected from C$_1$-C$_6$ alkyl.

17. The compound according to claim 1, wherein
R$_4$ and R$_5$ each are independently selected from: H, —COR$_7$, —SO$_2$R$_8$, and —SiR$_9$R$_{10}$R$_{11}$;
wherein, R$_7$ is selected from —CH$_3$; R$_8$ is selected from —CF$_3$, and p-methyl phenyl; R$_9$, R$_{10}$ and R$_{11}$ are independently selected from methyl, and tert-butyl.

18. The following compound, selected from:

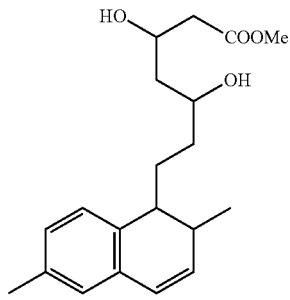

Compound 5 and diacetate, bis(4-methylbenzenesulfonate), bis(trifluoromethanesulfonate), and bis(tert-butyldimethylsilyl ether) of Compound 5;

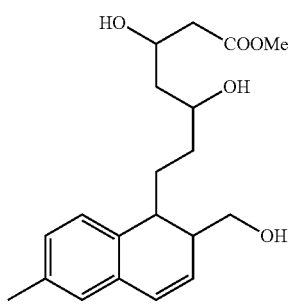 [SMILES: COC(=O)CC(O)CC(O)CCC1c2ccc(C)cc2C=CC1CO]

Compound 5a and triacetate, tri(4-methylbenzenesulfonate), tri(trifluoromethanesulfonate), and tri(tert-butyldimethylsilyl ether) of Compound 5a.

19. A pharmaceutical composition, comprising the compound according to claim 1 and optionally, a pharmaceutically acceptable excipient.

20. A method for inhibiting HMG-CoA reductase activity comprising contacting the compound according to claim 1 with HMG-CoA reductase.

21. A method for treating dyslipidemia, hyperlipemia, or atherosclerosis in a patient, comprising administering a therapeutically effective amount of the compound according to claim 1 to the patient in need of treatment.

22. A method for extracting Compound 5 from Monascus-fermented rice or extract thereof, comprising the following steps of:

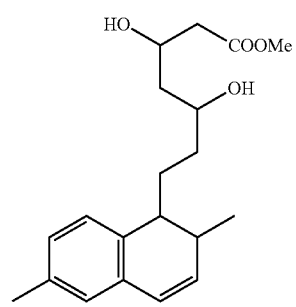

Compound 5

1) extracting Monascus-fermented rice or extract thereof with ethyl acetate (or dichloromethane or methanol or ethanol, or methanol/ethanol aqueous solution) as a solvent;
2) separating the ethyl acetate (or dichloromethane or methanol or ethanol, or methanol/ethanol aqueous solution) extract obtained in Step 1) by silica gel column chromatography, and carrying out gradient elution with petroleum ether, ethyl acetate and methanol, to obtain the ethyl acetate eluting fraction;
3) separating the ethyl acetate eluting fraction obtained in Step 2) by silica gel column chromatography, carrying out elution with dichloromethane-ethyl acetate-methanol, detecting and combining the fractions, to obtain the fractions in Step 3);
4) separating the second fraction obtained in Step 3) by C18 column chromatography, and carrying out gradient elution with acetonitrile-methanol-water, to obtain 82% (acetonitrile-methanol 1:1) aqueous solution eluting fraction;

5) further separating the 82% (acetonitrile-methanol 1:1) aqueous solution eluting fraction obtained in Step 4) by sephadex LH-20 column chromatography using dichloromethane-methanol as a mobile phase, analyzing and combining the fractions, to obtain the fractions in Step 5); and
6) purifying the third fraction obtained in Step 5) by chromatographic method, to obtain Compound 5.

23. The method according to claim 22, wherein,
1) extracting Monascus-fermented rice or extract thereof with 2-6-fold volume of ethyl acetate (or dichloromethane or methanol or ethanol, or methanol/ethanol aqueous solution) as a solvent for three times, 20-40 min for each time, combining the extracting solution, and concentrating it under reduced pressure to recover the solvent, and to obtain the ethyl acetate extract;
2) separating the ethyl acetate (or dichloromethane or methanol or ethanol, or methanol/ethanol aqueous solution) extract obtained in Step 1) by silica gel column chromatography, and carrying out gradient elution with petroleum ether, ethyl acetate and methanol or ethanol, or methanol/ethanol aqueous solution, to obtain the ethyl acetate eluting fraction;
3) separating the ethyl acetate eluting fraction obtained in Step 2) by silica gel column chromatography, carrying out elution with dichloromethane-ethyl acetate-methanol (30:30:1), and combining the fractions, to obtain 5 fractions;
4) separating the second fraction obtained in Step 3) by C18 column chromatography, and carrying out gradient elution with 82% (acetonitrile-methanol 1:1) aqueous solution ~100% (acetonitrile-methanol 1:1), to obtain 82% (acetonitrile-methanol 1:1) aqueous solution eluting fraction;
5) further separating the 82% (acetonitrile-methanol 1:1) aqueous solution eluting fraction obtained in Step 4) by sephadex LH-20 column chromatography using dichloromethane-methanol (2:1) as a mobile phase, and combining the fractions, to obtain 6 fractions in Step 5); and
6) purifying the third fraction obtained in Step 5) by chromatography using acetonitrile-methanol-water as a mobile phase and using C18 chromatographic column as a stationary phase, to obtain Compound 5

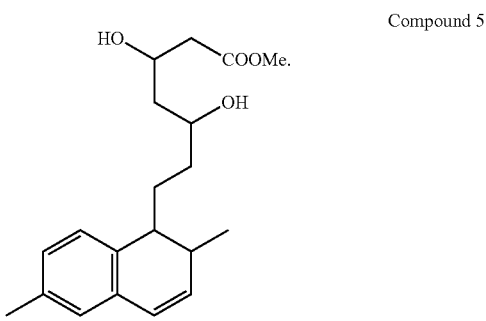 [SMILES: COC(=O)CC(O)CC(O)CCC1c2ccc(C)cc2C=CC1C]

Compound 5

24. A method for synthesizing the compound of Formula (I) according to claim 1:
reacting a compound of Formula (II) under alkaline condition, or adding an esterification reagent under alkaline condition, to prepare the compound of Formula (I), 29
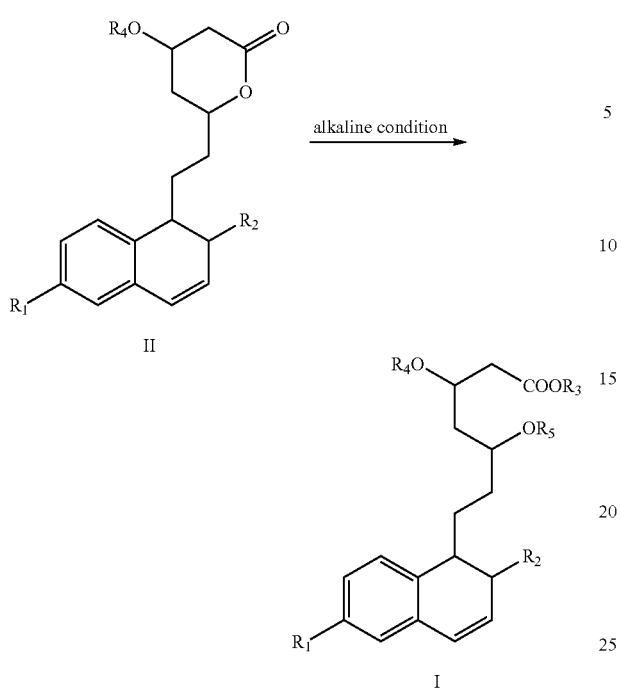
wherein, in Formula (II), $R_1$, $R_2$ and $R_4$ have the same meanings as defined in Formula (I) according to claim 1, and
wherein the pH range of the alkaline condition is 7.5-14.
25. A method for synthesizing compound 5:
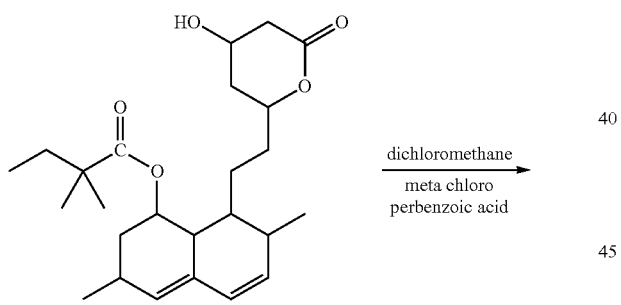
30
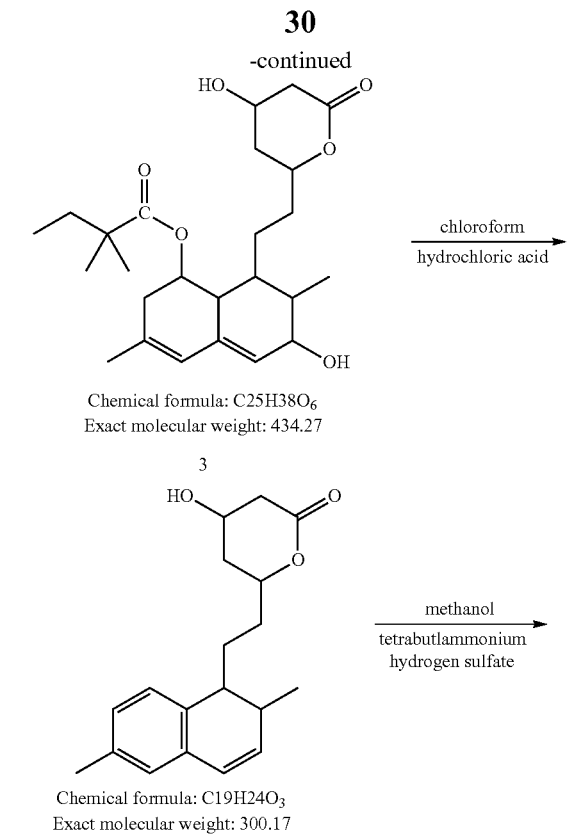
26. A method for synthesizing Compound 5:
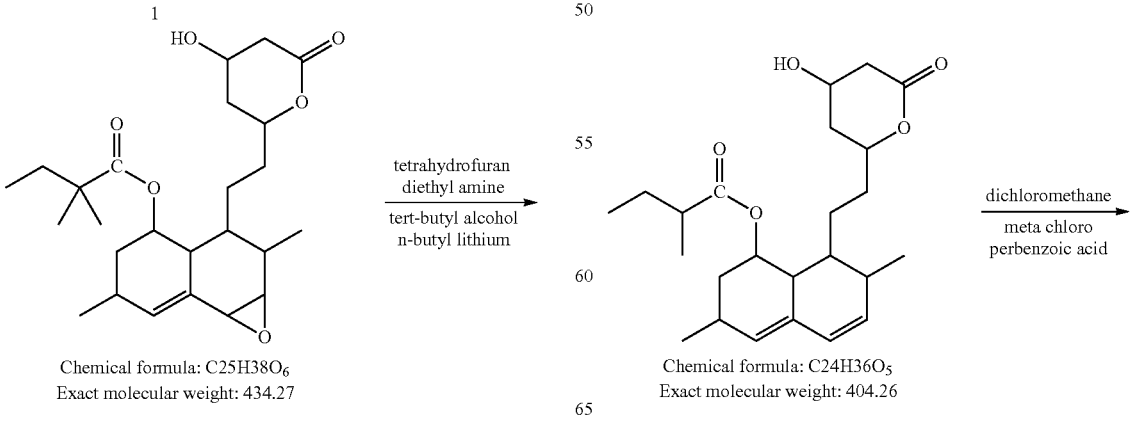

-continued

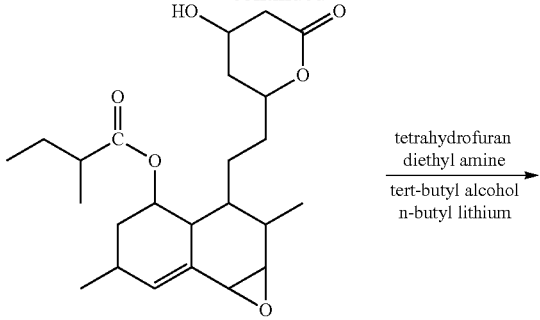

Chemical formula: C24H36O6
Exact molecular weight: 420.25

2b

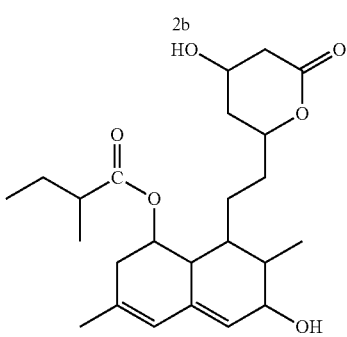

Chemical formula: C24H36O6
Exact molecular weight: 420.25

3b

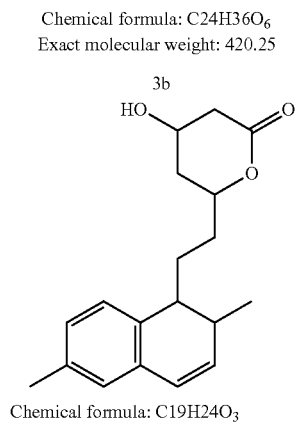

Chemical formula: C19H24O3
Exact molecular weight: 300.17

4

-continued

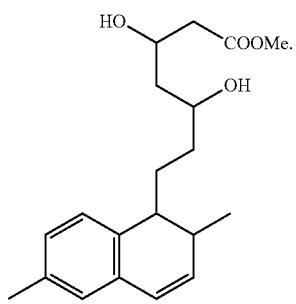

Chemical formula: C20H28O4
Exact molecular weight: 332.20

5

27. A method for treating hypercholesterolemia or combined hyperlipidemia in a patient, comprising administering a therapeutically effective amount of the compound according to claim 1 to the patient in need of treatment.

28. The method of claim 24 further comprising adding an alkaline reagent or a solvent.

29. The method of claim 28 wherein the alkaline reagent is selected from sodium hydroxide, potassium hydroxide, ammonia water and sodium carbonate.

30. The method of claim 24, wherein the esterification reagent is selected from lower alcohols, anhydrides, acyl chlorides, and chlorosilanes.

31. The method of claim 30, wherein the esterification reagent is a lower alcohol and the lower alcohol is selected from methanol and ethanol.

32. The method of claim 30, wherein the esterification reagent is an anhydride and the anhydride is selected from acetic anhydride, sulfonic anhydride, trifluoromethanesulfonic anhydride.

33. The method of claim 30, wherein the esterification reagent is an acyl chloride and the acyl chloride is toluenesulfonyl chloride.

34. The method of claim 30, wherein the esterification reagent is a chlorosilane and the chlorosilane is tert-butyldimethylchlorosilane.

* * * * *